(12) United States Patent
Liu et al.

(10) Patent No.: US 8,383,640 B2
(45) Date of Patent: Feb. 26, 2013

(54) SUBSTITUTED PYRIMIDINE ETHER COMPOUNDS AND USE THEREOF

(75) Inventors: Changling Liu, Shenyang (CN); Baoshan Chai, Shenyang (CN); Hong Zhang, Shenyang (CN); Huichao Li, Shenyang (CN); Junfeng Wang, Shenyang (CN); Yongwu Peng, Shenyang (CN); Jichun Yang, Shenyang (CN); Guangxin Liu, Shenyang (CN); Zhinian Li, Shenyang (CN)

(73) Assignees: Shenyang Research Institute of Chemical Industry Co., Ltd., Shenayang (CN); Sinochem Corporation, Beijing (CN)

( * ) Notice: Subject to any disclaimer, the term of this patent is extended or adjusted under 35 U.S.C. 154(b) by 0 days.

(21) Appl. No.: 12/597,173

(22) PCT Filed: May 22, 2008

(86) PCT No.: PCT/CN2008/071042
§ 371 (c)(1),
(2), (4) Date: Oct. 23, 2009

(87) PCT Pub. No.: WO2008/145052
PCT Pub. Date: Dec. 4, 2008

(65) Prior Publication Data
US 2010/0113490 A1    May 6, 2010

(30) Foreign Application Priority Data
May 25, 2007  (CN) .......................... 2007 1 0011434

(51) Int. Cl.
*A61K 31/505* (2006.01)
(52) U.S. Cl. ........................................... 514/272
(58) Field of Classification Search ............. None
See application file for complete search history.

(56) References Cited

U.S. PATENT DOCUMENTS

| | | | |
|---|---|---|---|
| 5,106,852 A | 4/1992 | Schuetz | |
| 5,935,965 A | 8/1999 | Kirstgen | |
| 6,114,342 A * | 9/2000 | Oberdorf et al. | 514/269 |

FOREIGN PATENT DOCUMENTS

| | | | |
|---|---|---|---|
| EP | 0513580 A | 11/1992 | |
| WO | WO 2005/123054 | * 12/2005 | |

OTHER PUBLICATIONS

STN Search Report ((Accession No. 2006:1186353) summarizing Liu et al (Nongyaoxue Xeubao 7:357-360, 2005).*
Williams et al (Foye's Principles of Medicinal Chemistrty, 5th Edition, pp. 59-63, 2002).*
Patani et al (Chem Rev 96:3147-3176, 1996).*
International Search Report mailed Sep. 4, 2008 in PCT/CN2008/071042.

* cited by examiner

*Primary Examiner* — Craig Ricci
(74) *Attorney, Agent, or Firm* — Smith, Gambrell & Russell, LLP

(57) ABSTRACT

The invention relates to substituted pyrimidine ether compounds having general formula I:

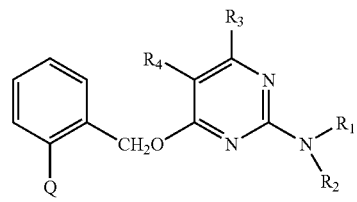

The groups are as defined as specification.

The compounds of formula I show high insecticidal activities for imagoes, larvae and nits of harmful acari and insects in the agricultural, civil and zoic fields, especially show excellent insecticidal activities for harmful acari such as *Tetranychus cinnabarinus*. Good effects can be obtained at very low dose. The compounds also exhibit preferably fungicidal activity. Wherefore, the invention also comprises the uses of compounds of formula I as insecticides, acaricides and/or fungicides in agricultural and other fields.

4 Claims, No Drawings

SUBSTITUTED PYRIMIDINE ETHER COMPOUNDS AND USE THEREOF

FIELD OF THE INVENTION

The invention relates to insecticide, acaricide, fungicide. Specifically to substituted pyrimidine ether compounds and use thereof.

BACKGROUND OF THE INVENTION

Methoxyacrylate compounds are natural products and known with biological activity. Methoxyacrylate compounds with insecticidal and acaricidal activities were reported as follows: EP242081, EP299694, EP335519, US2006235075, etc. In addition, strobilurins containing pyrimidine moiety also show insecticidal, acaricidal and fungicidal activity:

The following compounds with insecticidal activity were known in U.S. Pat. No. 5,106,852:

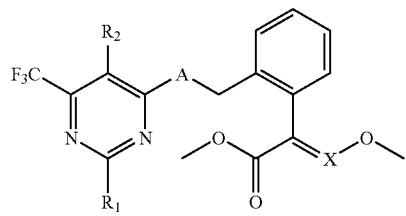

Wherein: $R_1$ is selected from alkyl, cycloalkyl, haloalkyl, alkoxy, alkylthio, substituted or unsubstituted aryl.

The following compound with fungicidal activity was disclosed in U.S. Pat. No. 5,378,711:

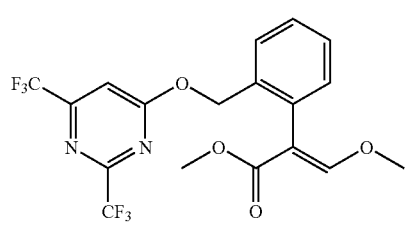 [SMILES: CO/C=C(/C(=O)OC)c1ccccc1COc1cc(C(F)(F)F)nc(C(F)(F)F)n1]

The following compounds with acaricidal, fungicidal activity were known in U.S. Pat. No. 5,935,965:

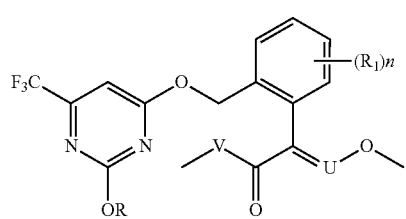

The following compounds with insecticidal, fungicidal activity were known in U.S. Pat. No. 6,114,342:

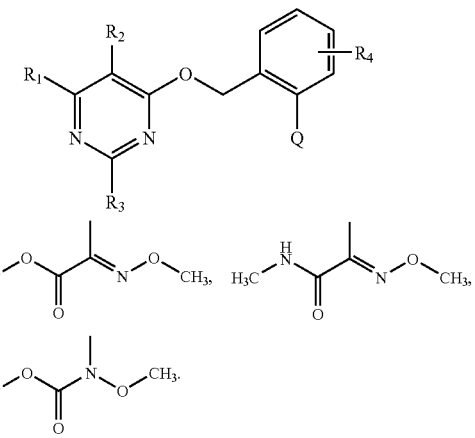

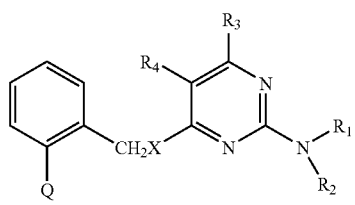

The compounds disclosed above patents (applications) were similar to this invention, but there are some obvious differences in structures.

SUMMARY OF THE INVENTION

The aim of the present invention is to provide the substituted pyrimidine ether compounds with biological activity against all sorts of plant disease and insects at very low dosage and the compounds can be applied in agriculture to control disease and insects in plant.

Detailed description of the invention is as follows:

The present invention offeres substituted pyrimidine ether compounds having general formula I:

I

Wherein:
$R_1$ and $R_2$ may be the same or different, selected from H, CN, $C_1$-$C_{12}$alkyl, $C_1$-$C_{12}$haloalkoyl, $C_1$-$C_{12}$alkoxy, $C_1$-$C_{12}$haloalkoxy, $C_3$-$C_6$cycloalkyl, $C_1$-$C_{12}$cyanoalkyl, $C_1$-$C_{12}$alkylamino, $C_1$-$C_{12}$haloalkylamino, $C_2$-$C_6$dialkylamino, $C_1$-$C_{12}$alkylthio, $C_1$-$C_{12}$haloalkylthio, $C_1$-$C_{12}$alkylsulfonyl, $C_1$-$C_{12}$alkylcarbonyl, $C_1$-$C_{12}$haloalkyl carbonyl, $C_1$-$C_{12}$haloalkylsulfonyl, $C_1$-$C_{12}$alkoxy$C_1$-$C_{12}$alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, 2,3-(methylenedioxy)phenyl, 3,4-(methylenedioxy)phenyl, 2,3-(difluoromethylenedioxy)phenyl, 3,4-(difluoromethylenedioxy)phenyl, 2,3-dihydro-1H-indoline-4-yl, 5,6,7,8-tetrahydronaphthalene-1-yl, phenylcarbonyl, benzylcarbonyl, phenylamino, phenylaminocarbonyl, phenylcarbonylaminocarbonyl, phenyl, benzyl or heteroaromatic rings; each phenylcarbonyl, benzylcarbonyl, phenylamino, phenylaminocarbonyl, phenylcarbonylaminocarbonyl, phenyl, benzyl and heteroaromatic ring optionally substituted with 1-5 substituents independently selected from the group consisting of halogen, $NO_2$, CN, $CONH_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylcarbonyl, $C_1$-$C_2$alkoxycarbonyl, $C_2$-$C_{12}$alkenyl, $C_2$-$C_{12}$haloalkenyl, $C_2$-$C_{12}$ alkenyloxy, $C_2$-$C_{12}$haloalkenyloxy, $C_2$-$C_{12}$alkynyl, $C_2$-$C_{12}$haloalkynyl, $C_2$-$C_{12}$alkylnyloxy, $C_2$-$C_{12}$haloalkynyloxy, $C_1$-$C_{12}$haloalkylthio, $C_1$-$C_{12}$haloalkylcarbonyl, $C_1$-$C_{12}$alkylamino, $C_1$-$C_{12}$haloalkylamino, $C_2$-$C_6$dialkylamino, $C_1$-$C_{12}$alkylcarbonylamino, $C_1$-$C_{12}$haloalkylcarbonylamino or $R_5$;

Or $NR_1R_2$ can join together to form 5- or 6-membered ring;

$R_3$ and $R_4$ may be the same or different, selected from H, halogen, $NO_2$, CN, $C_1$-$C_{12}$alkyl, $C_1$-$C_2$haloalkyl, $C_3$-$C_6$cycloalkyl, $C_1$-$C_{12}$alkoxy; $C_1$-$C_{12}$haloalkoxy, $C_1$-$C_{12}$alkylthio, $C_1$-$C_{12}$alkylsulfonyl, $C_1$-$C_{12}$ alkylcarbonyl, $C_1$-$C_{12}$ alkoxy$C_1$-$C_{12}$ alkyl, $C_1$-$C_{12}$alkoxycarbonyl, $C_1$-$C_{12}$alkoxycarbonyl$C_1$-$C_{12}$alkyl, $C_1$-$C_{12}$haloalkoxy$C_1$-$C_{12}$alkyl, phenyl, benzyl or heteroaromatic rings; each phenyl, benzyl and heteroaromatic ring optionally substituted with 1-5 substituents independently selected from the group consisting of halogen, $NO_2$, CN, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$alkylcarbonyl, $C_1$-$C_{12}$alkoxycarbonyl or $R_3$ and $R_4$ join together to form 5- or 6-membered ring;

$R_5$ is selected from phenyl, benzyl, phenoxy or benzyloxy; each phenyl, benzyl, phenoxy and benzyloxy optionally substituted with 1-5 substituents independently selected from the group consisting of halogen, $C_1$-$C_6$alkyl, $C_1$-$C_6$haloalkyl, $C_1$-$C_6$alkoxy or $C_1$-$C_6$haloalkoxy;

X is selected from O or S;

Q is selected from one of the following group:

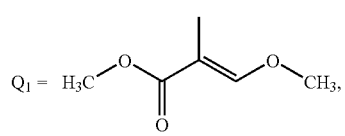

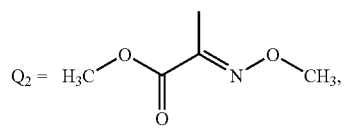

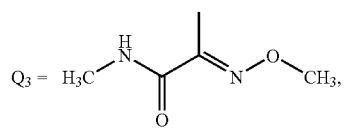

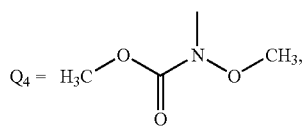

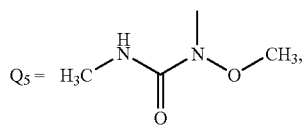

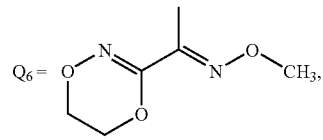

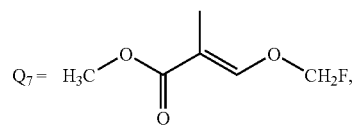

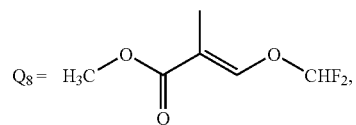

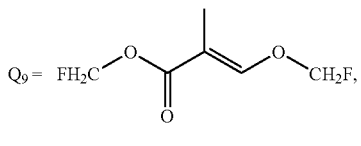

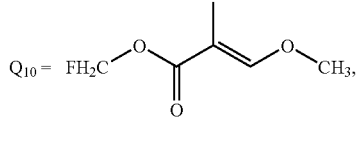

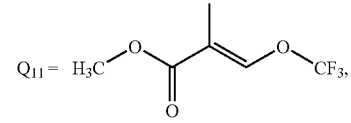

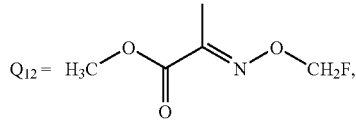

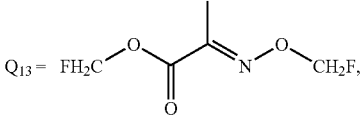

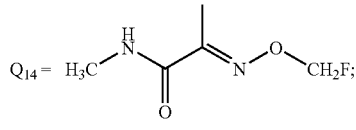

Or their salts, or stereoisomer.

The preferred compounds of general formula I of this invention are:

$R_1$ and $R_2$ may be the same or different, selected from H, CN, $C_1$-$C_6$alkyl, $C_1$-$C_6$haloalkyl, $C_1$-$C_6$alkoxy, $C_1$-$C_6$haloalkoxy, $C_3$-$C_6$cycloalkyl, $C_1$-$C_6$cyanoalkyl, $C_1$-$C_6$alkylamino, $C_1$-$C_6$haloalkylamino, $C_2$-$C_6$dialkylamino, $C_1$-$C_6$alkylthio, $C_1$-$C_6$alkylsulfonyl, $C_1$-$C_6$alkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, 2,3-(methylenedioxy)phenyl, 3,4-(methylenedioxy)phenyl, 2,3-(difluoromethylenedioxy)phenyl, 3,4-(difluoromethylenedioxy)phenyl, 2,3-dihydro- 1H-indoline-4-yl, 5,6,7,8-tetrahythonaphthalene-1-yl, 2,3-dihydro-1H-indoline-4-yl, 5,6,7,8-tetrahydronaphthalene-1-yl, phenylcarbonyl, benzylcarbonyl, phenylamino, phenylaminocarbonyl, phenylcarbonylaminocarbonyl, phenyl, benzyl, pyridyl, thienyl, thiazolyl, benzothiazolyl or pyrazolyl; each phenylcarbonyl, benzylcarbonyl, phenylamino, phenylaminocarbonyl, phenylcarbonylaminocarbonyl, phenyl, benzyl, pyridyl, thienyl, thiazolyl, benzothiazolyl and pyrazolyl optionally substituted with 1-5 substituents independently selected from the group consisting of halogen, $NO_2$, CN, $C_1$-$C_6$alkyl, $C_1$-$C_6$haloalkyl, $C_1$-$C_6$alkoxy; $C_1$-$C_6$haloalkoxy, $C_1$-$C_6$alkylthio, $C_1$-$C_6$alkylcarbonyl, $C_1$-$C_6$alkoxycarbonyl, $C_3$-$C_6$alkenyl, $C_3$-$C_6$haloalkenyl, $C_3$-$C_6$alkenyloxy, $C_3$-$C_6$haloalkenyloxy, $C_3$-$C_6$alkynyl, $C_3$-$C_6$haloalkynyl, $C_3$-$C_6$alkynyloxy, $C_3$-$C_6$haloalkynyloxy, $C_1$-$C_6$haloalkylthio, $C_1$-$C_6$haloalkylcarbonyl, $C_1$-$C_6$alkylamino, $C_1$-$C_6$haloalkylamino, $C_2$-$C_6$dialkylamino, $C_1$-$C_6$alkylcarbonylamino, $C_1$-$C_6$haloalkylcarbonylamino or $R_5$;

Or $NR_1R_2$ can join together to form morpholine, piperidine, pyrrolidine or piperazine;

$R_3$ and $R_4$ may be the same or different, selected from H, halogen, $NO_2$, CN, $C_1$-$C_6$alkyl, $C_1$-$C_6$haloalkyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfonyl, $C_1$-$C_6$alkylcarbonyl, $C_1$-$C_6$alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, phenyl, benzyl, pyridyl, thienyl, thiazolyl or pyrazolyl; each phenyl, benzyl, pyridyl, thienyl, thiazolyl and pyrazolyl optionally substituted with 1-3 substituents independently selected from the group consisting of halogen, $NO_2$, CN, $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$ alkylcarbonyl, $C_1$-$C_6$alkoxycarbonyl or $R_3$ and $R_4$ join together to form 5- or 6-membered ring;

$R_5$ is selected from phenyl, benzyl, phenoxy or benzyloxy; each phenyl, benzyl, phenoxy and benzyloxy optionally substituted with 1-5 substituents independently selected from the group consisting of: halogen, $C_1$-$C_4$alkyl, $C_1$-$C_3$haloalkyl, $C_1$-$C_3$alkoxy or $C_1$-$C_3$haloalkoxy;

X is selected from O or S;

Q is selected from one of the following group: $Q_1$-$Q_{14}$;

Or their salts are formed with hydrochlorides, phosphates, acetic acid, benzenesulfonic acid or oxalic acid.

Furthermore, the prepared compounds of general formula I of this invention are:
$R_1$ and $R_2$ may be the same or different, selected from H, CN, $C_1$-$C_4$alkyl, $C_1$-$C_3$haloalkyl, $C_1$-$C_3$alkoxy, $C_1$-$C_3$haloalkoxy, $C_3$-$C_6$cycloalkyl, $C_1$-$C_3$cyanoalkyl, $C_1$-$C_6$alkylamino, $C_1$-$C_3$haloalkylamino, $C_2$-$C_6$dialkylamino, $C_1$-$C_3$ alkylsulfonyl, $C_1$-$C_3$ alkylcarbonyl, $C_1$-$C_3$alkoxy$C_1$-$C_3$ alkyl, $C_1$-$C_3$alkoxycarbonyl, $C_1$-$C_3$haloalkoxy$C_1$-$C_3$alkyl, phenylcarbonyl, benzylcarbonyl, phenylamino, phenylaminocarbonyl, phenylcarbonylaminocarbonyl, phenyl, benzyl, pyridyl, thienyl, thiazolyl or benzothiazolyl; each phenylcarbonyl, benzylcarbonyl, phenylamino, phenylaminocarbonyl, phenylcarbonylaminocarbonyl, phenyl, benzyl, pyridyl, thienyl, thiazolyl and benzothiazolyl optionally substituted with 1-3 substituents independently selected from the group consisting of halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$ alkylthio, $C_1$-$C_3$alkylcarbonyl or $C_1$-$C_3$alkoxycarbonyl;

Or $NR_1R_2$ can join together to form morpholine, piperidine, pyrrolidine or piperazine;

$R_3$ and $R_4$ may be the same or different, selected from H, Cl, Br, $NO_2$, CN, $C_1$-$C_4$alkyl, $C_1$-$C_4$haloalkyl, $C_3$-$C_6$cycloalkyl, $C_1$-$C_3$alkoxy, $C_1$-$C_3$haloalkoxy, $C_1$-$C_3$alkylthio, $C_1$-$C_3$alkylsulfonyl, $C_1$-$C_3$alkoxy$C_1$-$C_3$alkyl, $C_1$-$C_3$haloalkoxy $C_1$-$C_3$alkyl, phenyl, benzyl, pyridyl, thienyl, thiazolyl or pyrazolyl; each phenyl, benzyl, pyridyl, thienyl, thiazolyl and pyrazolyl optionally substituted with 1-3 substituents independently selected from the group consisting of halogen, $NO_2$, CN, $C_1$-$C_3$alkyl, $C_1$-$C_3$haloalkyl, $C_1$-$C_3$alkoxy, $C_1$-$C_3$haloalkoxy, $C_1$-$C_3$ alkylthio, $C_1$-$C_3$alkylcarbonyl, $C_1$-$C_3$ alkoxycarbonyl;

X is selected from O or S;

Q is selected from one of the following group: $Q_1$-$Q_9$;

Or their salts are formed with hydrochlorides, phosphates, acetic acid, benzenesulfonic acid or oxalic acid.

Even more prepared compounds of general formula I of this invention are:
$R_1$ is selected from H or $C_1$-$C_4$ alkyl;
$R_2$ is selected from H, CN, $C_1$-$C_4$alkyl, $C_1$-$C_3$haloalkyl, $C_1$-$C_3$alkoxy, $C_1$-$C_3$haloalkoxy, $C_3$-$C_6$cycloalkyl, $C_1$-$C_3$cyanoalkyl, $C_1$-$C_4$alkylamino, $C_1$-$C_3$haloalkylamino, $C_2$-$C_6$dialkylamino, $C_1$-$C_3$alkylsulfonyl, $C_1$-$C_3$alkylcarbonyl, $C_1$-$C_3$alkoxycarbonyl, $C_1$-$C_3$alkoxy$C_1$-$C_2$alkyl, phenylcarbonyl, benzylcarbonyl, phenylamino, phenylaminocarbonyl, phenylcarbonylaminocarbonyl, phenyl, benzyl, pyridyl, thiazolyl or benzothiazolyl; each phenylcarbonyl, benzylcarbonyl, phenylamino, phenylaminocarbonyl, phenylcarbonylaminocarbonyl, phenyl, benzyl, pyridyl, thiazolyl and benzothiazolyl optionally substituted with 1-3 substituents independently selected from the group consisting of halogen, $NO_2$, CN, $C_1$-$C_3$alkyl, $C_1$-$C_3$ haloalkyl, $C_1$-$C_3$ alkoxy, $C_1$-$C_3$haloalkoxy, $C_1$-$C_3$alkylthio or $C_1$-$C_3$ alkoxycarbonyl;

Or $NR_1R_2$ can join together to form morpholine, piperidine, pyrrolidine or piperazine;

$R_3$ is selected from H, Cl, Br, F, $C_1$-$C_4$alkyl, $C_3$-$C_6$cycloalkyl, $CF_3$, $C_1$-$C_3$alkoxy, $C_1$-$C_3$haloalkoxy, $C_1$-$C_3$alkoxy$C_1$-$C_3$alkyl, $C_1$-$C_3$haloalkoxy$C_1$-$C_3$alkyl, phenyl or pyridyl; each phenyl and pyridyl optionally substituted with 1-3 substituents independently selected from the group consisting of Cl, Br, F, $NO_2$, CN, $C_1$-$C_3$alkoxy or $C_1$-$C_3$haloalkoxy;

$R_4$ is selected from H, Cl, Br, F, $OCH_3$, $OCF_3$, $SCH_3$, $SO_2CH_3$, $NHCH_3$, $CH_3$, CN, $OCH_2CF_3$, $CO_2C_2H_5$, phenyl, benzyl or pyridyl; each phenyl, benzyl and pyridyl optionally substituted with 1-3 substituents independently selected from the group consisting of Cl, Br, F, $NO_2$, CN, $C_1$-$C_3$alkyl, $CF_3$, $C_1$-$C_3$alkoxy or $C_1$-$C_3$ alkylthio;

X is selected from O or S;

Q is selected from one of the following group: $Q_1$-$Q_5$;

Or their salts are formed with hydrochlorides, phosphates, acetic acid, benzenesulfonic acid or oxalic acid.

The most prepared compounds of general formula I of this invention are:
$R_1$ is selected from H or $C_1$-$C_4$alkyl;
$R_2$ is selected from H, CN, $C_1$-$C_4$alkyl, $C_1$-$C_3$haloalkyl, $C_1$-$C_3$alkoxy, $C_1$-$C_3$haloalkoxy, $C_3$-$C_6$cycloalkyl, phenyl, benzyl, pyridyl, thiazolyl or benzothiazolyl; each phenyl, benzyl, pyridyl, thiazolyl and benzothiazolyl optionally substituted with 1-3 substituents independently selected from the group consisting of Cl, Br, F, $NO_2$, CN, $C_1$-$C_3$alkyl, $C_1$-$C_3$haloalkyl, $C_1$-$C_3$alkoxy or $C_1$-$C_3$haloalkoxy;

Or $NR_1R_2$ can join together to form morpholine, piperidine, pyrrolidine or piperazine;

$R_3$ is selected from H, Cl, Br, F, $C_1$-$C_4$alkyl, cyclopropyl, $CF_3$, $C_1$-$C_3$alkoxy, $C_1$-$C_3$haloalkoxy, $C_1$-$C_3$alkoxy$C_1$-$C_3$alkyl or $C_1$-$C_3$haloalkoxy $C_1$-$C_3$alkyl;

$R_4$ is selected from H, Cl, Br, F, $CH_3$, $OCH_3$ or CN;

X is selected from O or S;

Q is selected from one of the following group: $Q_1$-$Q_5$.

The following is the meaning of terms in the general formula I:

Halogen or halo is fluorine, chlorine, bromine or iodine.

The alkyl is to be understood as meaning straightchain or branched alkyl, such as methyl, ethyl, propyl, isopropyl or tert-butyl.

The cycloalkyl is unsubstituted or optionally substituted cyclic alkyl, such as cyclopropyl, cyclopentyl or cyclohexyl. The substituted group is methyl or halogen.

The haloalkyl refers to straight or branched chain alkyl, in which hydrogen atoms may be all or partly substituted with halogen, such as chloromethyl, dichloromethyl, trichloromethyl, fluoromethyl, difluoromethyl, trifluoromethyl.

The alkoxy refers to straight or branched chain alkyl, which is linked to the structure by oxygen atom.

The haloalkoxy refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy or trifluoroethoxy.

The alkylthio refers to straight or branched chain alkyl, which is linked to the structure by sulfur atom.

The haloalkylthio refers to straight or branched chain alkylthio, in which hydrogen atoms may be all or partly substituted with halogen, such as chloromethanethiol, dichloromethanethiol, trichloromethanethiol, fluoromethanethiol, difluoromethanethiol, trifluoromethanethiol, or chlorofluoromethanethiol.

The aryl and aryl in arylalkyl, aryloxy and aryloxyalkyl include phenyl or naphthyl.

The hetero aryl in this invention refers to five-membered ring or six-membered ring containing one or more N, O, S hetero atoms, such as pyridine, furan, pyrimidine, pyrazine, pyridazine, triazine, quinoline, thiazolyl, benzothiazolyl or benzofuran.

Because of the C=C or C=N links to different substituted group, the compounds of the invention may form geometrical isomers (the different isomers are respectively expressed with Z and E). Z isomer and E isomer and their mixtures in any proportion are included in the invention.

The group $R_2$ in general formula I refer to Table 1-8. When $R_2$ is pyridinyl, which substituted groups refer to Table 1-3. When $R_2$ is thiazolyl, which substituted groups refer to Table 4. When $R_2$ is phenyl, which substituted groups refer to Table 5. When $R_2$ is benzyl, which substituted groups refer to Table 6. When $NR_1R_2$ join together to form ring, the compounds refer to Table 7. When $R_2$ is other groups, which substituted groups refer to Table 8. The other groups in general formula I, such as $R_1$, $R_3$, $R_4$, X and Q, are defined as above.

TABLE 1

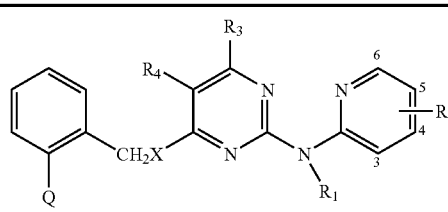

| R | R | R | R | R |
|---|---|---|---|---|
| H | 3-Br | 6-$OCH_3$ | 3-$CH_3$-5-$NO_2$ | 6-$CH_3$-3,5-2Br |
| 3-$CH_3$ | 4-Br | 5-$OCH_3$ | 4-$CH_3$-3-$NO_2$ | 3-$CONH_2$-4,6-2Cl |

TABLE 1-continued

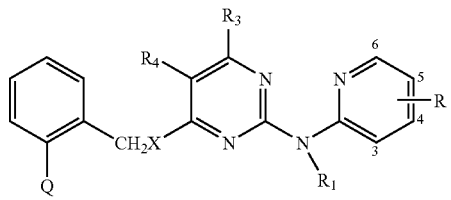

| R | R | R | R | R |
|---|---|---|---|---|
| 4-$CH_3$ | 5-Br | 3,5-2Cl | 4-$CH_3$-5-$NO_2$ | 4-$CH_3$-5-$NO_2$-3-Br |
| 5-$CH_3$ | 6-Br | 3,5-2Br | 5-$CH_3$-5-$NO_2$ | 3-CN-4,6-2Cl |
| 6-$CH_3$ | 5-I | 4-$CH_3$-5-Br | 6-$CH_3$-4-$NO_2$ | 3-CN-4-$CH_3$-6-Cl |
| 3-Cl | 5-F | 6-$CH_3$-5-CN | 6-$CH_3$-5-$NO_2$ | 3-CN-4-$CF_3$-6-Cl |
| 4-Cl | 6-F | 3,5,6-3Cl | 3-$NO_2$-5-Cl | 4-$CH_3$-5-CN-6-Cl |
| 5-Cl | 3-CN | 3-$CO_2CH_3$ | 3-$NO_2$-5-Br | 4-$CF_3$-5-CN-6-Cl |
| 6-Cl | 4-CN | 5-$CO_2CH_3$ | 5-$NO_2$-3-Br | 3-$CO_2CH_3$-6-Cl |
| 3-$CF_3$ | 5-CN | 3-$OCH_2Ph$ | 5-$CH_3$-3-Br | 5-$CO_2CH_3$-6-Cl |
| 4-$CF_3$ | 6-CN | 5-$CF_3$-3-Cl | 6-$CH_3$-5-Br | 5-$CF_3$-3,6-2Cl |
| 5-$CF_3$ | 3-$NO_2$ | 5-CN-3-Cl | 3-$CH_3$-5-Br | 5-$CF_3$-6-Cl |
| 6-$CF_3$ | 5-$NO_2$ | 5-$CH_3$-3-Cl | 3-$CF_3$-6-Cl | 3-CN-6-Cl |

TABLE 2

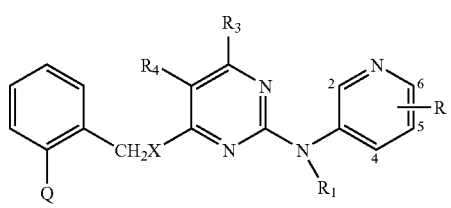

| R | R | R | R | R |
|---|---|---|---|---|
| H | 2-$OCH_3$ | 4-$CH_3$-2-Cl | 4-$CF_3$-2,6-2Cl | 6-OPh-3,5-2$CH_3$-4-Cl |
| 2-Cl | 6-$OCH_3$ | 5-$CH_3$-2-Cl | 4-$CH_3$-2,6-2Cl | 6-$OCH_3$-2-Cl |
| 6-Cl | 6-OPh | 6-$CH_3$-2-Cl | 6-OPh-4-Br | 6-$NHCH_3$-5-Cl |
| 2-Br | 2,6-2Cl | 2-OPh-6-Cl | 2-$OCH_2CF_3$ | 6-$SO_2CH_3$-5-Cl |
| 6-Br | 5,6-2Cl | 6-SPh-2,5-2Cl | 4-$CH_3$ |  |
| 6-Ph | 2,5-2Cl | 4-$CF_3$ | 6-$CF_3$ | 2-N |

TABLE 3

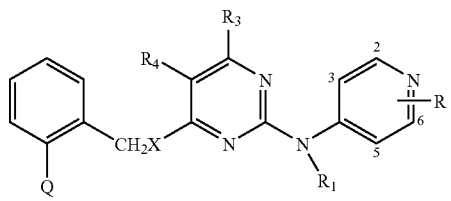

| R | R | R | R | R |
|---|---|---|---|---|
| H | 3-Cl | 2-$OCH_3$ | 2,6-2Cl | 2-$OCH_3$-6-Cl |
| 2-Cl | 2-Br | 2,6-2$OCH_3$ | 6-OPh | 2-$NHCH_3$-6-Cl |

TABLE 4

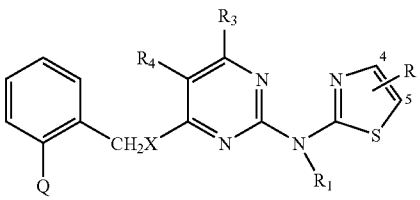

| R | R | R | R | R |
|---|---|---|---|---|
| H | 5-NO$_2$ | 4-CO$_2$C$_2$H$_5$ | 4-CH$_3$-5-COCH$_3$ | 4-(Ph-4-Cl)-5-CO$_2$C$_2$H$_5$ |
| 5-Cl | 5-OPh | 4-(Ph-3,4-2F) | 4-CH$_3$-5-CO$_2$C$_2$H$_5$ | 4,5-(CH=CH—CH=CH—) |
| 5-CH$_3$ | 5-OCH$_3$ | 4-(Ph-4-Cl) | 4-CF$_3$-5-CO$_2$C$_2$H$_5$ | 4,5-(CH=CH—CH=CH—) |
| 4-Cl | 4,5-2Cl | 4,5-(CH$_2$—)$_3$ | 5-CH$_3$-4-CO$_2$C$_2$H$_5$ | 4,5-(CH=CH—CH=CH—) |
| 5-Br | 4,5-2CH$_3$ | 4,5-(CH$_2$—)$_4$ | 5-Ph-4-CO$_2$C$_2$H$_5$ | 4,5-(CMe=CH—CH=CH—) |
| 4-CH$_3$ | 4-C(CH$_3$)$_3$ | 4-CF$_3$-5-CN | 4-CH$_3$-5-CONHCH$_3$ | 4,5-(CH=CMe—CH=CH—) |
| 5-Ph | 5-(Ph-4-Cl) | 4-CH$_2$CO$_2$C$_2$H$_5$ | 4-CF$_3$-5-CONHCH$_3$ | 4,5-(C(OMe)=CH—CH=CH—) |
| 4-Ph | 4-(Ph-4-Br) | 4-Ph-5-CO$_2$C$_2$H$_5$ | 4,5-(CH=CH—CH=CH—) | 4,5-(CH=C(OMe)—CH=CH—) |

TABLE 5

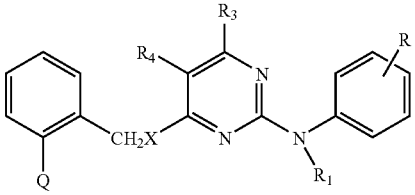

| R | R | R | R | R | R | R |
|---|---|---|---|---|---|---|
| H | 2-NO$_2$ | 2-SO$_2$C$_2$H$_5$ | 2,3-2F | 2,3-2CH$_3$ | 2-Cl-4-F | 4-CH$_3$-2-Br |
| 2-F | 3-NO$_2$ | 3-SO$_2$C$_2$H$_5$ | 2,4-2F | 2,4-2CH$_3$ | 2-Cl-4-Br | 4-CH$_3$-2-Cl |
| 3-F | 4-NO$_2$ | 4-SO$_2$C$_2$H$_5$ | 2,5-2F | 2,5-2CH$_3$ | 2-Cl-4-I | 2,4,6-3CH$_3$ |
| 4-F | 2-SCF$_3$ | 2-CO$_2$CH$_3$ | 2,6-2F | 2,6-2CH$_3$ | 3-Cl-4-I | 2,4,6-3C$_2$H$_5$ |
| 2-Cl | 3-SCF$_3$ | 3-CO$_2$CH$_3$ | 3,4-2F | 3,4-2CH$_3$ | 4-Cl-2-Br | 2-NHCOCH$_3$ |
| 3-Cl | 4-SCF$_3$ | 4-CO$_2$CH$_3$ | 3,5-2F | 3,5-2CH$_3$ | 3,4,5-3F | 3-NHCOCH$_3$ |
| 4-Cl | 2-OC$_2$H$_5$ | 2-CO$_2$C$_2$H$_5$ | 2,3-2Cl | 2,3-2C$_2$H$_5$ | 2,3,4-Cl | 4-NHCOCH$_3$ |
| 2-Br | 3-OC$_2$H$_5$ | 3-CO$_2$C$_2$H$_5$ | 2,4-2Cl | 2,4-2C$_2$H$_5$ | 2,3,5-Cl | 2-NHSO$_2$CH$_3$ |
| 3-Br | 4-OC$_2$H$_5$ | 4-CO$_2$C$_2$H$_5$ | 2,5-2Cl | 2,5-2C$_2$H$_5$ | 2,3,6-Cl | 3-NHSO$_2$CH$_3$ |
| 4-Br | 2-COCH$_3$ | 2-N(CH$_3$)2 | 2,6-2Cl | 2,6-2C$_2$H$_5$ | 2,4,5-Cl | 4-NHSO$_2$CH$_3$ |
| 2-I | 3-COCH$_3$ | 3-N(CH$_3$)2 | 3,4-2Cl | 3,4-2C$_2$H$_5$ | 2,4,6-Cl | 2-(Ph-4-Cl) |
| 3-I | 4-COCH$_3$ | 4-N(CH$_3$)2 | 3,5-2Cl | 3,5-2C$_2$H$_5$ | 3,4,5-Cl | 3-(Ph-4-Cl) |
| 4-I | 2-CH$_2$Ph | 2-N(C$_2$H$_5$)2 | 2,3-2Br | 2,3-2CF$_3$ | 2,3,4-3Br | 4-(Ph-4-Cl) |
| 2-CH$_3$ | 3-CH$_2$Ph | 3-N(C$_2$H$_5$)2 | 2,4-2Br | 2,4-2CF$_3$ | 2,3,5-3Br | 2-CH(CH$_3$)$_2$ |
| 3-CH$_3$ | 4-CH$_2$Ph | 4-N(C$_2$H$_5$)2 | 2,5-2Br | 2,5-2CF$_3$ | 2,3,6-3Br | 3-CH(CH$_3$)$_2$ |
| 4-CH$_3$ | 2-C(CH$_3$)$_3$ | 4-Ph | 2,6-2Br | 2,6-2CF$_3$ | 2,4,5-3Br | 4-CH(CH$_3$)$_2$ |
| 2-C$_2$H$_5$ | 3-C(CH$_3$)$_3$ | 2-OPh | 3,4-2Br | 3,4-2CF$_3$ | 2,4,6-3Br | 2-CF$_3$-4-Cl |
| 3-C$_2$H$_5$ | 4-C(CH$_3$)$_3$ | 3-OPh | 3,5-2Br | 3,5-2CF$_3$ | 3,4,5-3Br | 2-CF$_3$-4-Br |
| 4-C$_2$H$_5$ | 2-COCH$_3$ | 4-OPh | 2,3-2CN | 2,6-2SCF$_3$ | 4-CH$_3$-3-F | 3-CF$_3$-4-NO$_2$ |
| 2-CF$_3$ | 3-COCH$_3$ | 2,3-2OCH$_3$ | 2,4-2CN | 3,4-2SCF$_3$ | 4-CH$_3$-3-Cl | 3-CF$_3$-4-F |
| 3-CF$_3$ | 4-COCH$_3$ | 2,4-2OCH$_3$ | 2,5-2CN | 3,5-2SCF$_3$ | 4-CH$_3$-3-Br | 3-CF$_3$-4-Cl |
| 4-CF$_3$ | 2-COC$_2$H$_5$ | 2,5-2OCH$_3$ | 2,6-2CN | 2,3-2SCH$_3$ | 2,4,6-3CF$_3$ | 4-CF$_3$-2-NO$_2$ |
| 2-OCH$_3$ | 3-COC$_2$H$_5$ | 2,6-2OCH$_3$ | 3,4-2CN | 2,4-2SCH$_3$ | 2-CH$_3$-3-F | 4-CF$_3$-2-Cl |
| 3-OCH$_3$ | 4-COC$_2$H$_5$ | 3,4-2OCH$_3$ | 3,5-2CN | 2,5-2SCH$_3$ | 2-CH$_3$-3-Cl | 4-CF$_3$-2-Br |
| 4-OCH$_3$ | 2-SOCH$_3$ | 3,5-2OCH$_3$ | 2-F-4-Cl | 2,6-2SCH$_3$ | 2-CH$_3$-4-F | 2-CH$_3$-5-NO$_2$ |
| 2-SCH$_3$ | 3-SOCH$_3$ | 3-CONH$_2$ | 2-F-4-Br | 3,4-2SCH$_3$ | 2-CH$_3$-4-Cl | 2-CH$_3$-3-NO$_2$ |
| 3-SCH$_3$ | 4-SOCH$_3$ | 4-CONH$_2$ | 2-F-4-I | 3,5-2SCH$_3$ | 2-CH$_3$-4-Br | 2-SCH$_3$-5-Cl |
| 4-SCH$_3$ | 2-SO$_2$CH$_3$ | 2-OCH$_2$Ph | 2-F-5-Cl | 2,3-2OCF$_3$ | 2-CH$_3$-5-F | 4-SO$_2$CH$_3$-2Cl |
| 2-OCF$_3$ | 3-SO$_2$CH$_3$ | 3-OCH$_2$Ph | 3-F-5-Cl | 2,4-2OCF$_3$ | 2-CH$_3$-5-Cl | 2-CH$_3$-4-NO$_2$ |
| 3-OCF$_3$ | 4-SO$_2$CH$_3$ | 4-OCH$_2$Ph | 4-F-3-Cl | 2,5-2OCF$_3$ | 2-CH$_3$-5-Br | 2-CH$_3$-4-OCH$_3$ |
| 4-OCF$_3$ | 2-SOC$_2$H$_5$ | 2,3-NO$_2$ | 4-F-6-Cl | 2,6-2OCF$_3$ | 2-CH$_3$-6-Cl | 2-CH$_3$-6-C$_2$H$_5$ |
| 2-CN | 3-SOC$_2$H$_5$ | 2,4-NO$_2$ | 2,3,4-3F | 3,4-2OCF$_3$ | 3-CH$_3$-2-Br | 2-CH$_3$-6-NO$_2$ |
| 3-CN | 4-SOC$_2$H$_5$ | 2,5-2NO$_2$ | 2,3,5-3F | 3,5-2OCF$_3$ | 3-CH$_3$-4-Cl | 2,4,6-3NO$_2$ |
| 4-CN | 2-OCHF$_2$ | 2,6-2NO$_2$ | 2,3,6-3F | 2,3-2SCF$_3$ | 3-CH$_3$-4-Br | 2,3-2Cl-4-Br |
| 2-Ph | 3-OCHF$_2$ | 3,4-2NO$_2$ | 2,4,5-3F | 2,4-2SCF$_3$ | 3-CH$_3$-4-I | 2,4-2F-6-Cl |
| 3-Ph | 4-OCHF$_2$ | 3,5-2NO$_2$ | 2,4,6-3F | 2,5-2SCF$_3$ | 2-CH$_3$-4-I | 2-NO$_2$-4,6-2Br |

| R | R | R | R | R |
|---|---|---|---|---|
| 5-CF$_3$-2-Cl | 5-CF$_3$-2-OCH$_3$ | 4-CH$_3$-2,6-2Br | 3-CH$_3$-4-NHCOCH$_3$ | 2-NO$_2$-4-F |
| 5-CF$_3$-2-Br | 2-CF$_3$-4-NO$_2$ | 5-CH$_3$-4-F-6-Cl | 4-CH$_3$-3-NHSO$_2$CH$_3$ | 2-NO$_2$-4-Cl |
| 2-CN-3-F | 2,4-2NO$_2$-6-Cl | 4-C(CH$_3$)$_3$-2-Cl | 4-CH$_3$-3-OCH$_2$Ph-6-Br | 2-NO$_2$-4-Br |

TABLE 5-continued

| | | | | |
|---|---|---|---|---|
| 2-CN-3-Cl | 2,4-2NO$_2$-6-Br | 4-CF$_3$-2-Cl-6-Br | 5-CH$_3$-2-OCH$_3$-4-Cl | 2-NO$_2$-5-Cl |
| 2-CN-4-NO$_2$ | 2,3-2CH(CH$_3$)$_2$ | 2-COOCH$_3$-4-Br | 4-COCH$_3$-2,6-2Cl | 3-NO$_2$-4-Cl |
| 2-CN-4-Cl | 2,4-2CH(CH$_3$)$_2$ | 4-COOCH$_3$-2-Cl | 5-CF$_3$-2-NHCOCH$_3$ | 3-NO$_2$-4-Br |
| 2-CN-4-Br | 2,5-2CH(CH$_3$)$_2$ | 4-COOCH$_3$-2-Br | 2-CH$_3$-4-NO$_2$-6-Cl | 4-NO$_2$-2-Cl |
| 4-CN-2-CF$_3$ | 2,6-2CH(CH$_3$)$_2$ | 2,4,6-3CH(CH$_3$)$_2$ | 2-CH$_3$-4-NO$_2$-6-Br | 5-NO$_2$-2-Cl |
| 4-CN-2-Cl | 3,4-2CH(CH$_3$)$_2$ | 2,4,6-3C(CH$_3$)$_3$ | 2-CH$_3$-6-NO$_2$-4-Cl | 5-NO$_2$-2-Br |
| 4-CN-2-NO$_2$ | 3,5-2CH(CH$_3$)$_2$ | 2,3-2CH$_3$-6-NO$_2$ | 2-CH$_3$-6-NO$_2$-4-Br | 2-OCH$_3$-5-Cl |
| 5-CH$_3$-2-F | 2-NO$_2$-4-OCH$_3$ | 2,4-2OCH$_3$-5-Cl | 2,5-2OCH$_3$-4-NO$_2$ | 4-OCH$_3$-3-F |
| 4-CH$_3$-2-NO$_2$ | 2-NO$_2$-4-OC$_2$H$_5$ | 5-CONH$_2$-2-Cl | 2,6-2CH$_3$-4-C(CH$_3$)$_3$ | 4-OCH$_3$-3-Cl |
| 4-CH$_3$-3-NO$_2$ | 2,3-2C(CH$_3$)$_3$ | 4-N(CH$_3$)$_2$-2-NO$_2$ | 4-CF$_3$-2-NO$_2$-5-Cl | 3-NO$_2$-4-F |
| 5-CH$_3$-2-CN | 2,4-2C(CH$_3$)$_3$ | 5-N(CH$_3$)$_2$-2-NO$_2$ | 4-CF$_3$-2-NO$_2$-6-Cl | 2-OCF$_3$-4-CN |
| 5-NO2-2-F | 2,5-2C(CH$_3$)$_3$ | 4,5-2CH$_3$-2-NO$_2$ | 4-CF$_3$-2-NO$_2$-6-Br | 2-OCF$_3$-4-Cl |
| 2-CF$_3$-4,6-2Cl | 2,6-2C(CH$_3$)$_3$ | 2-NO$_2$-4-F-5-Cl | 5-CH$_3$-2-CONH$_2$ | 2-OCF$_3$-4-Br |
| 2-CF$_3$-4,6-2Br | 3,4-2C(CH$_3$)$_3$ | 2-CN-4-NO$_2$-6-Cl | 2-CH$_3$-5-CONH$_2$ | 2-F-4,6-2Br |
| 3-CH$_3$-2,6-2Cl | 3,5-2C(CH$_3$)$_3$ | 2-CN-4-NO$_2$-6-Br | 5-NHCOCH$_3$-2-Cl | 4-OCF$_3$-2-Cl |
| 2-CH$_3$-4,6-2Br | 4-SO$_2$NH$_2$ | 2-OCH$_2$CH=CH$_2$ | 4-O(CH$_2$)$_2$N(CH$_3$)$_2$ | 4-OCF$_3$-2-Br |
| 2,4,6-3OCH$_3$ | 4-NO$_2$-2-OCH$_3$ | 3-OCH$_2$CH=CH$_2$ | 4-CH$_3$-3-OCH$_2$Ph | 2,3,5,6-4F |
| 3,4,5-3OCH$_3$ | 2-CH$_2$CH=CH$_2$ | 4-OCH$_2$CH=CH$_2$ | 2-CH$_2$C(CH$_3$)=CH$_2$ | 2-CN-4,6-2Cl |
| 2,4,6-3SCH$_3$ | 3-CH$_2$CH=CH$_2$ | 2-OCH$_2$C≡CH | 3-CH$_2$C(CH$_3$)=CH$_2$ | 2-CN-4,6-2Br |
| 2,4,6-3OCF$_3$ | 4-CH$_2$CH=CH$_2$ | 3-OCH$_2$C≡CH | 4-CH$_2$C(CH$_3$)=CH$_2$ | 4-CN-2,6-2Cl |
| 2,4,6-3SCF$_3$ | 2-C(CH$_3$)=CH$_2$ | 4-OCH$_2$C≡CH | 4-O(CH$_2$)$_3$CH$_2$-2-NO$_2$ | 4-CF$_3$-2,6-2Cl |
| 2-CH$_2$C≡CH | 3-C(CH$_3$)=CH$_2$ | 5-NO$_2$-2-OCH$_3$ | 3-OCH$_3$-4-CO$_2$CH$_3$ | 4-CF$_3$-2,6-2Br |
| 3-CH$_2$C≡CH | 4-C(CH$_3$)=CH$_2$ | 5-CH$_3$-2-OCH$_3$ | 2-CH(CH$_3$)CH$_2$CH(CH$_3$)$_2$ | 2,3,4,5,6-5Cl |
| 4-CH$_2$C≡CH | 4-F-2,6-2Br | 4-NO$_2$-2,6-2Cl | 2,3-(CH$_2$CH$_2$CH$_2$—) | 2,3-(OCF$_2$O—) |
| 2-F-3-Cl | 2,4-2F-6-Cl | 4-OCF$_3$-2-NO$_2$ | 2,3-(CH$_2$CH$_2$CH$_2$CH$_2$—) | 2,3-(OCH$_2$O—) |
| 3-CH$_3$-2-Cl | 2-F-4-Cl-6-Br | 6-NO$_2$-2,3,4-3F | 4-NO$_2$-2,5-2Cl | 3,4-(OCH$_2$O—) |
| 4-O(CH$_2$)$_3$CH$_3$ | 2,3,5,6-4F-4-CF$_3$ | 4-NO$_2$-2,6-2Br | 4-F-3-Cl-2,6-2Br | 3,4-(OCF$_2$O—) |

TABLE 6

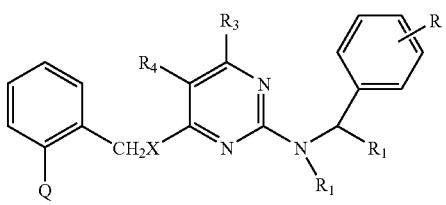

The group R in table 6 is defined as above in table 5.

TABLE 7

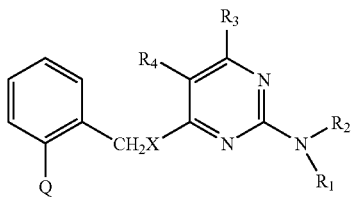

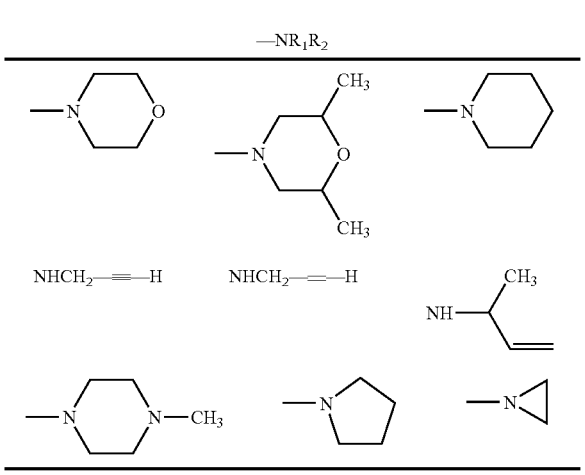

TABLE 8

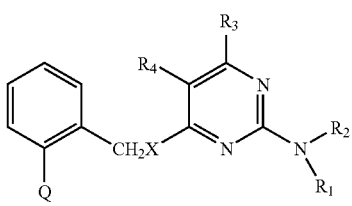

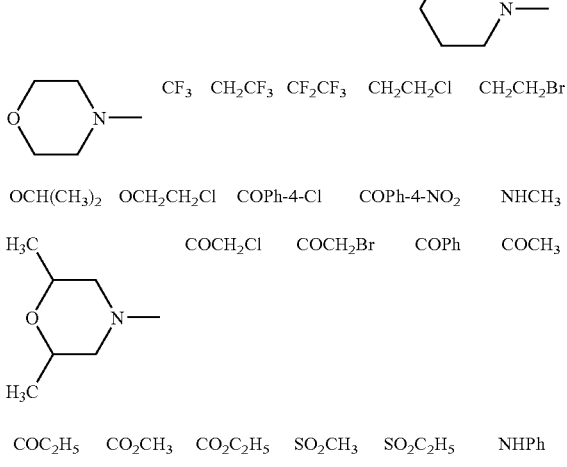

TABLE 8-continued

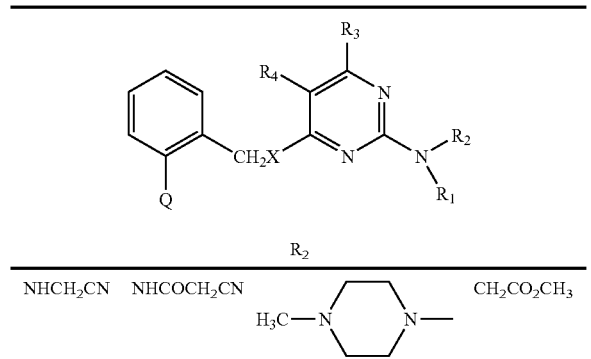

| R₂ | | | |
|---|---|---|---|
| NHCH₂CN | NHCOCH₂CN | H₃C—N⟨piperazine⟩N—CH₃ | CH₂CO₂CH₃ |
| CH₂CO₂C₂H₅ | CH₂C(CH₃)₂CH₃ | CH₂CH₂C(CH₃)₃ | CH(CH₃)CH₂CH₃ |

TABLE 8-continued

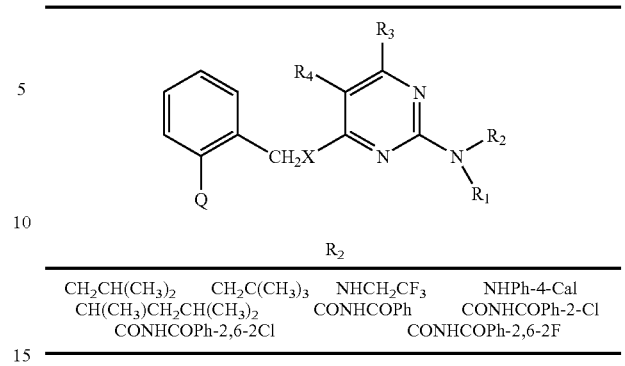

| R₂ | | | |
|---|---|---|---|
| CH₂CH(CH₃)₂ | CH₂C(CH₃)₃ | NHCH₂CF₃ | NHPh-4-Cal |
| CH(CH₃)CH₂CH(CH₃)₂ | | CONHCOPh | CONHCOPh-2-Cl |
| CONHCOPh-2,6-2Cl | | | CONHCOPh-2,6-2F |

The present invention is also explained by the following compounds in Table 9, but without being restricted thereby.

TABLE 9

I

| No. | X | R₁ | R₂ | R₃ | R₄ | Q |
|---|---|---|---|---|---|---|
| 1 | O | H | CH₃ | CH₃ | H | Q₁ |
| 2 | O | H | CH₃ | CF₃ | H | Q₁ |
| 3 | O | H | CH₃ | i-Pr | H | Q₁ |
| 4 | O | H | CH₃ | t-Bu | H | Q₁ |
| 5 | O | H | CH₃ | cyclopropyl | H | Q₁ |
| 6 | O | H | CH₃ | Ph | H | Q₁ |
| 7 | O | H | CH₃ | CH₃ | CH₃ | Q₁ |
| 8 | O | H | CH₃ | CF₃ | CH₃ | Q₁ |
| 9 | O | H | CH₃ | CF₃ | Cl | Q₁ |
| 10 | O | H | CH₃ | i-Pr | Cl | Q₁ |
| 11 | O | H | CH₃ | CH₃ | OCH₃ | Q₁ |
| 12 | O | H | CH₃ | CF₃ | OCH₃ | Q₁ |
| 13 | O | H | CH₃ | cyclopropyl | OCH₃ | Q₁ |
| 14 | O | H | CH₃ | Ph | OCH₃ | Q₁ |
| 15 | O | H | CH₃ | CH₃ | SCH₃ | Q₁ |
| 16 | O | H | CH₃ | CF₃ | SCH₃ | Q₁ |
| 17 | O | H | CH₃ | CH₃ | NHCH₃ | Q₁ |
| 18 | O | H | CH₃ | CF₃ | NHCH₃ | Q₁ |
| 19 | O | H | Ph | CH₃ | H | Q₁ |
| 20 | O | H | Ph | CF₃ | H | Q₁ |
| 21 | O | H | H | CH₃ | H | Q₁ |
| 22 | O | H | H | CF₃ | H | Q₁ |
| 23 | O | H | Ph | i-Pr | H | Q₁ |
| 24 | O | H | Ph | t-Bu | H | Q₁ |
| 25 | O | H | Ph | cyclopropyl | H | Q₁ |
| 26 | O | H | Ph | Ph | H | Q₁ |
| 27 | O | H | Ph | Ph-4-NO₂ | H | Q₁ |
| 28 | O | H | Ph | CH₂Ph-4-OCH₃ | H | Q₁ |
| 29 | O | H | Ph | Ph-2-CN | H | Q₁ |
| 30 | O | H | Ph | Ph-4-Cl | H | Q₁ |
| 31 | O | H | Ph | Cl | H | Q₁ |
| 32 | O | H | Ph | Br | H | Q₁ |
| 33 | O | H | Ph | OCH₃ | H | Q₁ |
| 34 | O | H | Ph | OCH₂CF₃ | H | Q₁ |
| 35 | O | H | Ph | SCH₃ | H | Q₁ |
| 36 | O | H | Ph | NHCH₃ | H | Q₁ |
| 37 | O | H | Ph | SO₂CH₃ | H | Q₁ |
| 38 | O | H | Ph | NO₂ | H | Q₁ |
| 39 | O | H | Ph | CN | H | Q₁ |
| 40 | O | H | Ph | COC₂H₅ | H | Q₁ |
| 41 | O | H | Ph | CH₃ | CH₃ | Q₁ |
| 42 | O | H | Ph | CF₃ | CH₃ | Q₁ |
| 43 | O | H | Ph | i-Pr | CH₃ | Q₁ |
| 44 | O | H | Ph | t-Bu | CH₃ | Q₁ |

TABLE 9-continued

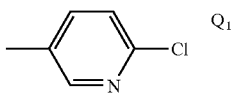

| No. | X | R₁ | R₂ | R₃ | R₄ | Q |
|---|---|---|---|---|---|---|
| 45 | O | H | Ph | cyclopropyl | $CH_3$ | $Q_1$ |
| 46 | O | H | Ph | Ph | $CH_3$ | $Q_1$ |
| 47 | O | H | Ph | $CH_3$ | Cl | $Q_1$ |
| 48 | O | H | Ph | $CF_3$ | Cl | $Q_1$ |
| 49 | O | H | Ph | i-Pr | Cl | $Q_1$ |
| 50 | O | H | Ph | t-Bu | Cl | $Q_1$ |
| 51 | O | H | Ph | cyclopropyl | Cl | $Q_1$ |
| 52 | O | H | Ph | Ph | Cl | $Q_1$ |
| 53 | O | H | Ph | $CH_3$ | Br | $Q_1$ |
| 54 | O | H | Ph | $CF_3$ | Br | $Q_1$ |
| 55 | O | H | Ph | i-Pr | Br | $Q_1$ |
| 56 | O | H | Ph | t-Bu | Br | $Q_1$ |
| 57 | O | H | Ph | cyclopropyl | Br | $Q_1$ |
| 58 | O | H | Ph | Ph | Br | $Q_1$ |
| 59 | O | H | Ph | $CH_3$ | $OCH_3$ | $Q_1$ |
| 60 | O | H | Ph | $CF_3$ | $OCH_3$ | $Q_1$ |
| 61 | O | H | Ph | i-Pr | $OCH_3$ | $Q_1$ |
| 62 | O | H | Ph | t-Bu | $OCH_3$ | $Q_1$ |
| 63 | O | H | Ph | cyclopropyl | $OCH_3$ | $Q_1$ |
| 64 | O | H | Ph | Ph | $OCH_3$ | $Q_1$ |
| 65 | O | H | Ph | $CH_3$ | $SCH_3$ | $Q_1$ |
| 66 | O | H | Ph | $CF_3$ | $SCH_3$ | $Q_1$ |
| 67 | O | H | Ph | $CH_3$ | $NHCH_3$ | $Q_1$ |
| 68 | O | H | Ph | $CF_3$ | $NHCH_3$ | $Q_1$ |
| 69 | O | H | Ph | $CH_3$ | $SO_2CH_3$ | $Q_1$ |
| 70 | O | H | Ph | $CF_3$ | $SO_2CH_3$ | $Q_1$ |
| 71 | O | H | Ph | $CF_3$ | $NO_2$ | $Q_1$ |
| 72 | O | H | Ph | $CF_3$ | CN | $Q_1$ |
| 73 | O | H | Ph | $CF_3$ | $CH_2Cl$ | $Q_1$ |
| 74 | O | H | Ph | $CF_3$ | $CH_2CH_2Cl$ | $Q_1$ |
| 75 | O | H | Ph | $CF_3$ | $OCH_2CF_3$ | $Q_1$ |
| 76 | O | H | Ph | $CF_3$ | $COC_2H_5$ | $Q_1$ |
| 77 | O | H | Ph | $CF_3$ | $CO_2C_2H_5$ | $Q_1$ |
| 78 | O | H | Ph | $CF_3$ | $CH_2OCH_2CF_3$ | $Q_1$ |
| 79 | O | H | Ph | $CF_3$ | Ph | $Q_1$ |
| 80 | O | H | Ph | $CF_3$ | Ph-4-Cl | $Q_1$ |
| 81 | O | H | Ph | $CF_3$ | Ph-2,4-2Cl | $Q_1$ |
| 82 | O | H | Ph | $CF_3$ | Ph-4-$CH_3$ | $Q_1$ |
| 83 | O | H | Ph | $CF_3$ | Ph-2-$CH_3$ | $Q_1$ |
| 84 | O | H | Ph | $CF_3$ | Ph-4-$NO_2$ | $Q_1$ |
| 85 | O | H | Ph | $CF_3$ | Ph-2,4-2$SCH_3$ | $Q_1$ |
| 86 | O | H | Ph | $CF_3$ | Ph-4-$OCH_3$ | $Q_1$ |
| 87 | O | H | Ph | $CF_3$ | Ph-2-CN | $Q_1$ |
| 88 | O | H | Ph | $CF_3$ | $CH_2$Ph | $Q_1$ |
| 89 | O | H | Ph | $CF_3$ | $CH_2$Ph-4-Cl | $Q_1$ |
| 90 | O | H | Ph | $CF_3$ | $CH_2$Ph-2,4-2Cl | $Q_1$ |
| 91 | O | H | Ph | $CF_3$ | $CH_2$Ph-4-$NO_2$ | $Q_1$ |
| 92 | O | H | Ph | $CF_3$ | $CH_2$Ph-4-$OCH_3$ | $Q_1$ |
| 93 | O | H | Ph | $CF_3$ | $CH_2$Ph-2-CN | $Q_1$ |
| 94 | O | H | Ph | $CF_3$ | 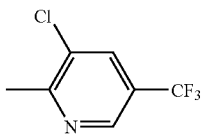 | $Q_1$ |
| 95 | O | H | Ph | $CF_3$ | 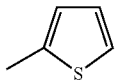 | $Q_1$ |
| 96 | O | H | Ph | $CF_3$ |  | $Q_1$ |

TABLE 9-continued

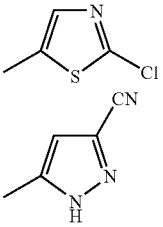

| No. | X | R₁ | R₂ | R₃ | R₄ | Q |
|---|---|---|---|---|---|---|
| 97 | O | H | Ph | CF₃ | 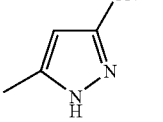 | Q₁ |
| 98 | O | H | Ph | CF₃ | | Q₁ |
| 99 | S | H | Ph | CH₃ | H | Q₁ |
| 100 | S | H | Ph | CF₃ | H | Q₁ |
| 101 | S | H | Ph | cyclopropyl | H | Q₁ |
| 102 | S | H | Ph | Ph | H | Q₁ |
| 103 | S | H | Ph | Cl | H | Q₁ |
| 104 | S | H | Ph | Br | H | Q₁ |
| 105 | O | H | Ph | OCH₃ | H | Q₁ |
| 106 | O | H | Ph | OCH₂CF₃ | H | Q₁ |
| 107 | S | H | Ph | SCH₃ | H | Q₁ |
| 108 | S | H | Ph | SO₂CH₃ | H | Q₁ |
| 109 | S | H | Ph | CH₃ | CH₃ | Q₁ |
| 110 | S | H | Ph | CF₃ | CH₃ | Q₁ |
| 111 | S | H | Ph | i-Pr | CH₃ | Q₁ |
| 112 | S | H | Ph | CH₃ | Cl | Q₁ |
| 113 | S | H | Ph | CF₃ | Cl | Q₁ |
| 114 | S | H | Ph | Ph | Cl | Q₁ |
| 115 | S | H | Ph | CF₃ | Br | Q₁ |
| 116 | S | H | Ph | CH₃ | OCH₃ | Q₁ |
| 117 | S | H | Ph | CF₃ | OCH₃ | Q₁ |
| 118 | S | H | Ph | CF₃ | OCH₂CF₃ | Q₁ |
| 119 | S | H | Ph | CF₃ | SCH₃ | Q₁ |
| 120 | S | H | Ph | CF₃ | NHCH₃ | Q₁ |
| 121 | S | H | Ph | CH₃ | SO₂CH₃ | Q₁ |
| 122 | S | H | Ph | CF₃ | SO₂CH₃ | Q₁ |
| 123 | S | H | Ph | CF₃ | CN | Q₁ |
| 124 | O | H | CH₂CH₂CH₃ | CF₃ | H | Q₁ |
| 125 | O | H | cyclopentanyl | CF₃ | H | Q₁ |
| 126 | O | H | benzothiazol-2-yl | CF₃ | H | Q₁ |
| 127 | O | H | thiazol-2-yl | CF₃ | H | Q₁ |
| 128 | S | H | Ph | CF₃ | CO₂C₂H₅ | Q₁ |
| 129 | S | H | Ph | CF₃ | Ph | Q₁ |
| 130 | S | H | Ph | CF₃ | Ph-4-Cl | Q₁ |
| 131 | S | H | Ph | CF₃ | Ph-4-NO₂ | Q₁ |
| 132 | S | H | Ph | CF₃ | Ph-2,4-2SCH₃ | Q₁ |
| 133 | S | H | Ph | CF₃ | Ph-4-OCH₃ | Q₁ |
| 134 | S | H | Ph | CF₃ | Ph-2-CN | Q₁ |
| 135 | S | H | Ph | CF₃ | CH₂Ph | Q₁ |
| 136 | S | H | Ph | CF₃ | CH₂Ph-4-Cl | Q₁ |
| 137 | S | H | Ph | CF₃ | CH₂Ph-2,4-2Cl | Q₁ |
| 138 | S | H | Ph | CF₃ | CH₂Ph-4-NO₂ | Q₁ |
| 139 | S | H | Ph | CF₃ | CH₂Ph-4-OCH₃ | Q₁ |
| 140 | S | H | Ph | CF₃ | CH₂Ph-2-CN | Q₁ |
| 141 | O | H | COCH₃ | CF₃ | H | Q₁ |
| 142 | O | H | COCH₃ | i-Pr | H | Q₁ |
| 143 | O | H | COCH₃ | cyclopropyl | H | Q₁ |
| 144 | O | H | COCH₃ | Ph | H | Q₁ |
| 145 | O | H | COCH₃ | CH₃ | CH₃ | Q₁ |
| 146 | O | H | COCH₃ | CF₃ | CH₃ | Q₁ |
| 147 | O | H | COCH₃ | CH₃ | Cl | Q₁ |
| 148 | O | H | COCH₃ | CF₃ | Cl | Q₁ |
| 149 | O | H | COCH₃ | CH₃ | OCH₃ | Q₁ |
| 150 | O | H | COCH₃ | CF₃ | OCH₃ | Q₁ |
| 151 | O | H | COCH₃ | CF₃ | OCH₂CF₃ | Q₁ |
| 152 | O | H | COCH₃ | CH₃ | SCH₃ | Q₁ |
| 153 | O | H | N=C(CH₃)₂ | CF₃ | H | Q₁ |

TABLE 9-continued

I

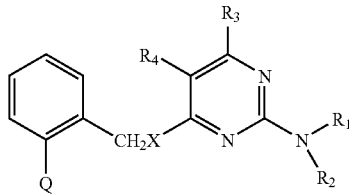

| No. | X | R₁ | R₂ | R₃ | R₄ | Q |
|---|---|---|---|---|---|---|
| 154 | O | H | N=C(CH$_3$)Ph-4-Cl | CF$_3$ | H | Q$_1$ |
| 155 | O | H | CH(CN)CH$_3$ | CF$_3$ | H | Q$_1$ |
| 156 | O | H | COCH$_2$Cl | CF$_3$ | H | Q$_1$ |
| 157 | O | H | COCH$_2$Cl | CF$_3$ | CH$_3$ | Q$_1$ |
| 158 | O | H | COCH$_2$Cl | CH$_3$ | Cl | Q$_1$ |
| 159 | O | H | COCH$_2$Cl | CF$_3$ | Br | Q$_1$ |
| 160 | O | H | COCH$_2$Cl | CF$_3$ | OCH$_3$ | Q$_1$ |
| 161 | O | H | COCH$_2$Cl | CH$_3$ | SCH$_3$ | Q$_1$ |
| 162 | O | H | CO$_2$C$_2$H$_5$ | CF$_3$ | H | Q$_1$ |
| 163 | O | H | CO$_2$C$_2$H$_5$ | CF$_3$ | CH$_3$ | Q$_1$ |
| 164 | O | H | CO$_2$C$_2$H$_5$ | CH$_3$ | Cl | Q$_1$ |
| 165 | O | H | CO$_2$C$_2$H$_5$ | CF$_3$ | Br | Q$_1$ |
| 166 | O | H | CO$_2$C$_2$H$_5$ | CF$_3$ | OCH$_3$ | Q$_1$ |
| 167 | O | H | CO$_2$C$_2$H$_5$ | CH$_3$ | SCH$_3$ | Q$_1$ |
| 168 | O | H | CH$_2$CO$_2$C$_2$H$_5$ | CF$_3$ | H | Q$_1$ |
| 169 | O | H | CH$_2$CO$_2$C$_2$H$_5$ | CF$_3$ | CH$_3$ | Q$_1$ |
| 170 | O | H | SO$_2$CH$_3$ | CF$_3$ | H | Q$_1$ |
| 171 | O | (CH$_2$)$_3$CH$_3$ | (CH$_2$)$_3$CH$_3$ | CF$_3$ | H | Q$_1$ |
| 172 | O | H | SO$_2$CH$_3$ | CH$_3$ | Cl | Q$_1$ |
| 173 | O | H | SO$_2$CH$_3$ | CF$_3$ | Br | Q$_1$ |
| 174 | O | H | SO$_2$CH$_3$ | CF$_3$ | OCH$_3$ | Q$_1$ |
| 175 | O | H | SO$_2$CH$_3$ | CH$_3$ | SCH$_3$ | Q$_1$ |
| 176 | O | CH$_3$ | SO$_2$CH$_3$ | CF$_3$ | H | Q$_1$ |
| 177 | O | CH$_3$ | SO$_2$CH$_3$ | CF$_3$ | CH$_3$ | Q$_1$ |
| 178 | O | CH$_3$ | SO$_2$CH$_3$ | CH$_3$ | Cl | Q$_1$ |
| 179 | O | CH$_3$ | SO$_2$CH$_3$ | CF$_3$ | Br | Q$_1$ |
| 180 | O | CH$_3$ | SO$_2$CH$_3$ | OCH$_2$CF$_3$ | Br | Q$_1$ |
| 181 | O | H | COPh | CF$_3$ | H | Q$_1$ |
| 182 | O | H | COPh | CF$_3$ | CH$_3$ | Q$_1$ |
| 183 | O | H | COPh-4-Cl | CH$_3$ | Cl | Q$_1$ |
| 184 | O | H | COPh-4-NO$_2$ | CF$_3$ | Br | Q$_1$ |
| 185 | O | H | CONHCOPh | CF$_3$ | H | Q$_1$ |
| 186 | O | H | CONHCOPh | CF$_3$ | OCH$_3$ | Q$_1$ |
| 187 | O | H | CONHCOPh-2,6-2F | CF$_3$ | SCH$_3$ | Q$_1$ |
| 188 | O | H | CONHCOPh-2-Cl | CF$_3$ | H | Q$_1$ |
| 189 | O | C$_2$H$_5$ | C$_2$H$_5$ | CH$_3$ | H | Q$_1$ |
| 190 | O | C$_2$H$_5$ | C$_2$H$_5$ | CF$_3$ | H | Q$_1$ |
| 191 | O | H | Ph-2-Cl | CF$_3$ | H | Q$_1$ |
| 192 | O | H | Ph-2-CH$_3$ | CF$_3$ | H | Q$_1$ |
| 193 | O | H | Ph-2-F | CF$_3$ | H | Q$_1$ |
| 194 | O | H | Ph-2-C$_2$H$_5$ | CF$_3$ | H | Q$_1$ |
| 195 | O | H | Ph-2-CH(CH$_3$)$_2$ | CF$_3$ | H | Q$_1$ |
| 196 | O | H | Ph-2-OCH$_3$ | CF$_3$ | H | Q$_1$ |
| 197 | O | H | Ph-2,3-(OCH$_2$O—) | CF$_3$ | H | Q$_1$ |
| 198 | O | C$_2$H$_5$ | C$_2$H$_5$ | CF$_3$ | OCH$_3$ | Q$_1$ |
| 199 | O | C$_2$H$_5$ | C$_2$H$_5$ | CF$_3$ | OCH$_2$CF$_3$ | Q$_1$ |
| 200 | O | C$_2$H$_5$ | C$_2$H$_5$ | CH$_3$ | SCH$_3$ | Q$_1$ |
| 201 | O | C$_2$H$_5$ | C$_2$H$_5$ | CF$_3$ | SCH$_3$ | Q$_1$ |
| 202 | O | C$_2$H$_5$ | C$_2$H$_5$ | CF$_3$ | NHCH$_3$ | Q$_1$ |
| 203 | O | i-Pr | Ph | Ph | H | Q$_1$ |
| 204 | O | i-Pr | Ph | CH$_3$ | CH$_3$ | Q$_1$ |
| 205 | O | i-Pr | Ph | CF$_3$ | H | Q$_1$ |
| 206 | O | i-Pr | Ph | CF$_3$ | Cl | Q$_1$ |
| 207 | O | i-Pr | Ph | CH$_3$ | OCH$_3$ | Q$_1$ |
| 208 | O | i-Pr | Ph | CF$_3$ | OCH$_3$ | Q$_1$ |
| 209 | O | H | NHCH$_3$ | CF$_3$ | H | Q$_1$ |
| 210 | O | H | NHCH$_2$CF$_3$ | CF$_3$ | H | Q$_1$ |
| 211 | O | H | OCH$_3$ | CF$_3$ | H | Q$_1$ |
| 212 | O | H | OC$_2$H$_5$ | CF$_3$ | H | Q$_1$ |
| 213 | O | H | NHPh | CF$_3$ | H | Q$_1$ |
| 214 | O | H | NHPh-4-Cl | CH$_3$ | H | Q$_1$ |
| 215 | O | H | NHCH$_2$Ph | CF$_3$ | H | Q$_1$ |
| 216 | O | H | CN | CF$_3$ | H | Q$_1$ |
| 217 | O | H | CH$_2$CN | CF$_3$ | H | Q$_1$ |
| 218 | O | H | CH$_2$CH$_2$Cl | CF$_3$ | H | Q$_1$ |
| 219 | O | H | N(CH$_3$)$_2$ | CF$_3$ | H | Q$_1$ |
| 220 | O | H | CH$_3$ | CH$_3$ | H | Q$_2$ |

TABLE 9-continued

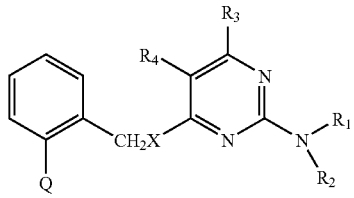

| No. | X | R₁ | R₂ | R₃ | R₄ | Q |
|---|---|---|---|---|---|---|
| 221 | O | H | CH₃ | CF₃ | H | Q₂ |
| 222 | O | H | CH₃ | CH₃ | CH₃ | Q₂ |
| 223 | O | H | CH₃ | CF₃ | CH₃ | Q₂ |
| 224 | O | H | CH₃ | CF₃ | Cl | Q₂ |
| 225 | O | H | CH₃ | i-Pr | Cl | Q₂ |
| 226 | O | H | CH₃ | CF₃ | OCH₃ | Q₂ |
| 227 | O | H | CH₃ | CF₃ | SCH₃ | Q₂ |
| 228 | O | H | CH₃ | CH₃ | NHCH₃ | Q₂ |
| 229 | O | H | Ph | CF₃ | H | Q₂ |
| 230 | O | H | Ph | i-Pr | H | Q₂ |
| 231 | O | H | Ph | t-Bu | H | Q₂ |
| 232 | O | H | Ph | cyclopropyl | H | Q₂ |
| 233 | O | H | Ph | Ph | H | Q₂ |
| 234 | O | H | Ph | Ph-4-NO₂ | H | Q₂ |
| 235 | O | H | Ph | CH₂Ph-4-OCH₃ | H | Q₂ |
| 236 | O | H | Ph | Ph-4-Cl | H | Q₂ |
| 237 | O | H | Ph | Cl | H | Q₂ |
| 238 | O | H | Ph | Br | H | Q₂ |
| 239 | O | H | Ph | OCH₃ | H | Q₂ |
| 240 | O | H | Ph | SCH₃ | H | Q₂ |
| 241 | O | H | Ph | NHCH₃ | H | Q₂ |
| 242 | O | H | Ph | SO₂CH₃ | H | Q₂ |
| 243 | O | H | Ph | NO₂ | H | Q₂ |
| 244 | O | H | Ph | CN | H | Q₂ |
| 245 | O | H | Ph | CF₃ | CH₃ | Q₂ |
| 246 | O | H | Ph | i-Pr | CH₃ | Q₂ |
| 247 | O | H | Ph | t-Bu | CH₃ | Q₂ |
| 248 | O | H | Ph | t-Bu | Cl | Q₂ |
| 249 | O | H | Ph | cyclopropyl | Cl | Q₂ |
| 250 | O | H | Ph | CH₃ | Br | Q₂ |
| 251 | O | H | Ph | CF₃ | Br | Q₂ |
| 252 | O | H | Ph | i-Pr | Br | Q₂ |
| 253 | O | H | Ph | CH₃ | OCH₃ | Q₂ |
| 254 | O | H | Ph | CF₃ | OCH₃ | Q₂ |
| 255 | O | H | Ph | CF₃ | SCH₃ | Q₂ |
| 256 | O | H | Ph | CH₃ | NHCH₃ | Q₂ |
| 257 | O | H | Ph | CF₃ | NHCH₃ | Q₂ |
| 258 | O | H | Ph | CH₃ | SO₂CH₃ | Q₂ |
| 259 | O | H | Ph | CF₃ | SO₂CH₃ | Q₂ |
| 260 | O | H | Ph | CF₃ | NO₂ | Q₂ |
| 261 | O | H | Ph | CF₃ | CN | Q₂ |
| 262 | O | H | Ph | CF₃ | CH₂Cl | Q₂ |
| 263 | O | H | Ph | CF₃ | CH₂CH₂Cl | Q₂ |
| 264 | O | H | Ph | CF₃ | OCH₂CF₃ | Q₂ |
| 265 | O | H | Ph | CF₃ | COC₂H₅ | Q₂ |
| 266 | O | H | Ph | CF₃ | CO₂C₂H₅ | Q₂ |
| 267 | O | H | Ph | CF₃ | CH₂OCH₂CF₃ | Q₂ |
| 268 | O | H | Ph | CF₃ | Ph | Q₂ |
| 269 | O | H | Ph | CF₃ | Ph-4-Cl | Q₂ |
| 270 | O | H | Ph | CF₃ | Ph-2,4-2Cl | Q₂ |
| 271 | O | H | Ph | CF₃ | Ph-4-CH₃ | Q₂ |
| 272 | O | H | Ph | CF₃ | Ph-2-CH₃ | Q₂ |
| 273 | O | H | Ph | CF₃ | Ph-4-NO₂ | Q₂ |
| 274 | O | H | Ph | CF₃ | Ph-2,4-2SCH₃ | Q₂ |
| 275 | O | H | Ph | CF₃ | Ph-4-OCH₃ | Q₂ |
| 276 | O | H | Ph | CF₃ | Ph-2-CN | Q₂ |
| 277 | O | H | Ph | CF₃ | CH₂Ph | Q₂ |
| 278 | O | H | Ph | CF₃ | CH₂Ph-4-Cl | Q₂ |
| 279 | O | H | Ph | CF₃ | CH₂Ph-2,4-2Cl | Q₂ |
| 280 | O | H | Ph | CF₃ | CH₂Ph-4-NO₂ | Q₂ |
| 281 | S | H | Ph | CH₃ | H | Q₂ |
| 282 | S | H | Ph | CF₃ | H | Q₂ |
| 283 | S | H | Ph | Br | H | Q₂ |
| 284 | S | H | Ph | OCH₃ | H | Q₂ |
| 285 | S | H | Ph | SCH₃ | H | Q₂ |
| 286 | S | H | Ph | SO₂CH₃ | H | Q₂ |
| 287 | S | H | Ph | CH₃ | CH₃ | Q₂ |

TABLE 9-continued

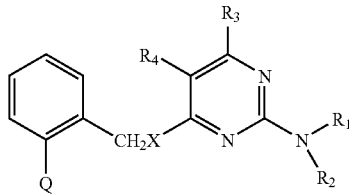

| No. | X | R₁ | R₂ | R₃ | R₄ | Q |
|---|---|---|---|---|---|---|
| 288 | S | H | Ph | CF₃ | CH₃ | Q₂ |
| 289 | S | H | Ph | i-Pr | CH₃ | Q₂ |
| 290 | S | H | Ph | Ph | Cl | Q₂ |
| 291 | S | H | Ph | CF₃ | Br | Q₂ |
| 292 | S | H | Ph | CH₃ | OCH₃ | Q₂ |
| 293 | S | H | Ph | CF₃ | SO₂CH₃ | Q₂ |
| 294 | S | H | Ph | CF₃ | CN | Q₂ |
| 295 | S | H | Ph | CF₃ | CH₂Cl | Q₂ |
| 296 | S | H | Ph | CF₃ | CH₂CH₂Cl | Q₂ |
| 297 | S | H | Ph | CF₃ | OCH₂CF₃ | Q₂ |
| 298 | S | H | Ph | CF₃ | COC₂H₅ | Q₂ |
| 299 | S | H | Ph | CF₃ | CO₂C₂H₅ | Q₂ |
| 300 | S | H | Ph | CF₃ | Ph | Q₂ |
| 301 | S | H | Ph | CF₃ | Ph-4-Cl | Q₂ |
| 302 | O | H | COCH₃ | CF₃ | H | Q₂ |
| 303 | O | H | COCH₃ | i-Pr | H | Q₂ |
| 304 | O | H | COCH₃ | cyclopropyl | H | Q₂ |
| 305 | O | H | COCH₃ | Ph | H | Q₂ |
| 306 | O | H | COCH₃ | CH₃ | CH₃ | Q₂ |
| 307 | O | H | COCH₃ | CF₃ | OCH₃ | Q₂ |
| 308 | O | H | COCH₃ | CH₃ | SCH₃ | Q₂ |
| 309 | O | H | COCH₃ | CF₃ | SCH₃ | Q₂ |
| 310 | O | H | COCH₃ | CF₃ | NHCH₃ | Q₂ |
| 311 | O | H | COCH₂Cl | CF₃ | H | Q₂ |
| 312 | O | H | COCH₂Cl | CF₃ | CH₃ | Q₂ |
| 313 | O | H | CO₂C₂H₅ | CF₃ | H | Q₂ |
| 314 | O | H | CO₂C₂H₅ | CF₃ | CH₃ | Q₂ |
| 315 | O | H | CO₂C₂H₅ | CH₃ | Cl | Q₂ |
| 316 | O | H | SO₂CH₃ | CF₃ | H | Q₂ |
| 317 | O | H | SO₂CH₃ | CF₃ | CH₃ | Q₂ |
| 318 | O | H | SO₂CH₃ | CH₃ | Cl | Q₂ |
| 319 | O | CH₃ | SO₂CH₃ | CF₃ | H | Q₂ |
| 320 | O | CH₃ | SO₂CH₃ | CF₃ | CH₃ | Q₂ |
| 321 | O | H | COPh | CF₃ | H | Q₂ |
| 322 | O | H | COPh | CF₃ | CH₃ | Q₂ |
| 323 | O | H | COPh-4-Cl | CH₃ | Cl | Q₂ |
| 324 | O | H | COPh-4-NO₂ | CF₃ | Br | Q₂ |
| 325 | O | H | CONHCOPh | CF₃ | H | Q₂ |
| 326 | O | H | CONHCOPh-2,6-2F | CF₃ | H | Q₂ |
| 327 | O | C₂H₅ | C₂H₅ | CH₃ | H | Q₂ |
| 328 | O | C₂H₅ | C₂H₅ | CF₃ | cyclopropyl | Q₂ |
| 329 | O | C₂H₅ | C₂H₅ | cyclopropyl | H | Q₂ |
| 330 | O | C₂H₅ | C₂H₅ | Ph | H | Q₂ |
| 331 | O | i-Pr | Ph | Ph | H | Q₂ |
| 332 | O | i-Pr | Ph | CH₃ | CH₃ | Q₂ |
| 333 | O | i-Pr | Ph | CF₃ | Cl | Q₂ |
| 334 | O | H | NHCH₃ | CF₃ | H | Q₂ |
| 335 | O | H | NHCH₂CF₃ | CF₃ | H | Q₂ |
| 336 | O | H | OCH₃ | CF₃ | H | Q₂ |
| 337 | O | H | OC₂H₅ | CF₃ | H | Q₂ |
| 338 | O | H | NHPh | CF₃ | H | Q₂ |
| 339 | O | H | NHPh-4-Cl | CH₃ | H | Q₂ |
| 340 | O | H | NHCH₂Ph | CF₃ | H | Q₂ |
| 341 | O | H | CN | CF₃ | H | Q₂ |
| 342 | O | H | CH₂CN | CF₃ | H | Q₂ |
| 343 | O | H | CH₂CH₂Cl | CF₃ | H | Q₂ |
| 344 | O | H | CH₂CH₂Cl | CF₃ | Br | Q₂ |
| 345 | O | H | CH₃ | CH₃ | H | Q₃ |
| 346 | O | H | CH₃ | CF₃ | H | Q₃ |
| 347 | O | H | CH₃ | CH₃ | CH₃ | Q₃ |
| 348 | O | H | CH₃ | CF₃ | CH₃ | Q₃ |
| 349 | O | H | CH₃ | CF₃ | Cl | Q₃ |
| 350 | O | H | CH₃ | i-Pr | Cl | Q₃ |
| 351 | O | H | Ph | CF₃ | H | Q₃ |
| 352 | O | H | Ph | i-Pr | H | Q₃ |
| 353 | O | H | Ph | Ph-4-NO₂ | H | Q₃ |
| 354 | O | H | Ph | CH₂Ph-4-OCH₃ | H | Q₃ |

TABLE 9-continued

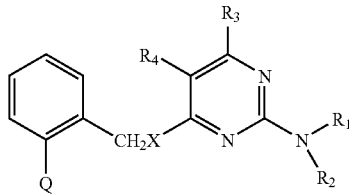

| No. | X | R₁ | R₂ | R₃ | R₄ | Q |
|---|---|---|---|---|---|---|
| 355 | O | H | Ph | Ph-4-Cl | H | Q₃ |
| 356 | O | H | Ph | Cl | H | Q₃ |
| 357 | O | H | Ph | Br | H | Q₃ |
| 358 | O | H | Ph | OCH₃ | H | Q₃ |
| 359 | O | H | Ph | NHCH₃ | H | Q₃ |
| 360 | O | H | Ph | SO₂CH₃ | H | Q₃ |
| 361 | O | H | Ph | NO₂ | H | Q₃ |
| 362 | O | H | Ph | CN | H | Q₃ |
| 363 | O | H | Ph | CF₃ | CH₃ | Q₃ |
| 364 | O | H | Ph | i-Pr | CH₃ | Q₃ |
| 365 | O | H | Ph | t-Bu | CH₃ | Q₃ |
| 366 | O | H | Ph | t-Bu | Cl | Q₃ |
| 367 | O | H | Ph | cyclopropyl | Cl | Q₃ |
| 368 | O | H | Ph | CF₃ | OCH₃ | Q₃ |
| 369 | O | H | Ph | CF₃ | SCH₃ | Q₃ |
| 370 | O | H | Ph | CH₃ | NHCH₃ | Q₃ |
| 371 | O | H | Ph | CF₃ | NHCH₃ | Q₃ |
| 372 | O | H | Ph | CH₃ | SO₂CH₃ | Q₃ |
| 373 | O | H | Ph | CF₃ | Ph-2-CH₃ | Q₃ |
| 374 | O | H | Ph | CF₃ | Ph-4-NO₂ | Q₃ |
| 375 | O | H | Ph | CF₃ | Ph-4-OCH₃ | Q₃ |
| 376 | O | H | Ph | CF₃ | Ph-2-CN | Q₃ |
| 377 | O | H | Ph | CF₃ | CH₂Ph | Q₃ |
| 378 | O | H | Ph | CF₃ | CH₂Ph-4-Cl | Q₃ |
| 379 | O | H | Ph | CF₃ | CH₂Ph-2,4-2Cl | Q₃ |
| 380 | O | H | Ph | CF₃ | CH₂Ph-4-NO₂ | Q₃ |
| 381 | S | H | Ph | CH₃ | H | Q₃ |
| 382 | S | H | Ph | CF₃ | H | Q₃ |
| 383 | S | H | Ph | CF₃ | CH₂CH₂Cl | Q₃ |
| 384 | S | H | Ph | CF₃ | OCH₂CF₃ | Q₃ |
| 385 | S | H | Ph | CF₃ | COC₂H₅ | Q₃ |
| 386 | S | H | Ph | CF₃ | CO₂C₂H₅ | Q₃ |
| 387 | S | H | Ph | CF₃ | Ph | Q₃ |
| 388 | S | H | Ph | CF₃ | Ph-4-Cl | Q₃ |
| 389 | O | H | COCH₃ | CF₃ | H | Q₃ |
| 390 | O | H | COCH₃ | i-Pr | H | Q₃ |
| 391 | O | H | COCH₃ | cyclopropyl | H | Q₃ |
| 392 | O | H | COCH₃ | Ph | H | Q₃ |
| 393 | O | H | COCH₃ | CF₃ | SCH₃ | Q₃ |
| 394 | O | H | COCH₃ | CF₃ | NHCH₃ | Q₃ |
| 395 | O | H | COCH₂Cl | CF₃ | H | Q₃ |
| 396 | O | H | COCH₂Cl | CF₃ | CH₃ | Q₃ |
| 397 | O | H | CO₂C₂H₅ | CF₃ | H | Q₃ |
| 398 | O | H | CO₂C₂H₅ | CF₃ | CH₃ | Q₃ |
| 399 | O | H | CO₂C₂H₅ | CH₃ | Cl | Q₃ |
| 400 | O | H | SO₂CH₃ | CF₃ | H | Q₃ |
| 401 | O | H | SO₂CH₃ | CF₃ | CH₃ | Q₃ |
| 402 | O | H | SO₂CH₃ | CH₃ | Cl | Q₃ |
| 403 | O | CH₃ | SO₂CH₃ | CF₃ | H | Q₃ |
| 404 | O | H | COPh | CF₃ | CH₃ | Q₃ |
| 405 | O | H | COPh-4-Cl | CH₃ | Cl | Q₃ |
| 406 | O | H | COPh-4-NO₂ | CF₃ | Br | Q₃ |
| 407 | O | H | CONHCOPh | CF₃ | H | Q₃ |
| 408 | O | H | CONHCOPh-2,6-2F | CF₃ | H | Q₃ |
| 409 | O | C₂H₅ | C₂H₅ | CH₃ | H | Q₃ |
| 410 | O | C₂H₅ | C₂H₅ | CF₃ | H | Q₃ |
| 411 | O | C₂H₅ | C₂H₅ | cyclopropyl | H | Q₃ |
| 412 | O | C₂H₅ | C₂H₅ | Ph | H | Q₃ |
| 413 | O | i-Pr | Ph | Ph | H | Q₃ |
| 414 | O | i-Pr | Ph | CH₃ | CH₃ | Q₃ |
| 415 | O | H | NHCH₂CF₃ | CF₃ | H | Q₃ |
| 416 | O | H | OCH₃ | CF₃ | H | Q₃ |
| 417 | O | H | NHPh-4-Cl | CH₃ | H | Q₃ |
| 418 | O | H | NHCH₂Ph | CF₃ | H | Q₃ |
| 419 | O | H | CN | CF₃ | H | Q₃ |
| 420 | O | H | CH₃ | CH₃ | H | Q₄ |
| 421 | O | H | CH₃ | CF₃ | H | Q₄ |

TABLE 9-continued

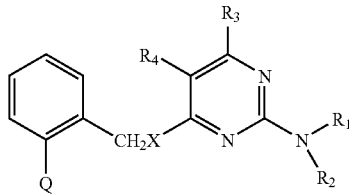

| No. | X | R₁ | R₂ | R₃ | R₄ | Q |
|---|---|---|---|---|---|---|
| 422 | O | H | CH₃ | CF₃ | CH₃ | Q₄ |
| 423 | O | H | CH₃ | i-Pr | Cl | Q₄ |
| 424 | O | H | Ph | CF₃ | H | Q₄ |
| 425 | O | H | Ph | Ph-4-NO₂ | H | Q₄ |
| 426 | O | H | Ph | CH₂Ph-4-OCH₃ | H | Q₄ |
| 427 | O | H | Ph | Ph-4-Cl | H | Q₄ |
| 428 | O | H | Ph | Cl | H | Q₄ |
| 429 | O | H | Ph | Br | H | Q₄ |
| 430 | O | H | Ph | OCH₃ | H | Q₄ |
| 431 | O | H | Ph | CF₃ | CH₃ | Q₄ |
| 432 | O | H | Ph | i-Pr | CH₃ | Q₄ |
| 433 | O | H | Ph | t-Bu | CH₃ | Q₄ |
| 434 | O | H | Ph | t-Bu | Cl | Q₄ |
| 435 | O | H | Ph | cyclopropyl | Cl | Q₄ |
| 436 | O | H | Ph | CF₃ | OCH₃ | Q₄ |
| 437 | O | H | Ph | CF₃ | NHCH₃ | Q₄ |
| 438 | O | H | Ph | CH₃ | SO₂CH₃ | Q₄ |
| 439 | O | H | Ph | CF₃ | Ph-2-CH₃ | Q₄ |
| 440 | O | H | Ph | CF₃ | Ph-4-NO₂ | Q₄ |
| 441 | O | H | Ph | CF₃ | CH₂Ph | Q₄ |
| 442 | O | H | Ph | CF₃ | CH₂Ph-4-Cl | Q₄ |
| 443 | S | H | Ph | CF₃ | H | Q₄ |
| 444 | S | H | Ph | CF₃ | CH₂CH₂Cl | Q₄ |
| 445 | S | H | Ph | CF₃ | OCH₂CF₃ | Q₄ |
| 446 | S | H | Ph | CF₃ | COC₂H₅ | Q₄ |
| 447 | S | H | Ph | CF₃ | CO₂C₂H₅ | Q₄ |
| 448 | S | H | Ph | CF₃ | Ph | Q₄ |
| 449 | S | H | Ph | CF₃ | Ph-4-Cl | Q₄ |
| 450 | O | H | COCH₃ | CF₃ | SCH₃ | Q₄ |
| 451 | O | H | COCH₃ | CF₃ | NHCH₃ | Q₄ |
| 452 | O | H | COCH₂Cl | CF₃ | H | Q₄ |
| 453 | O | H | COCH₂Cl | CF₃ | CH₃ | Q₄ |
| 454 | O | H | CO₂C₂H₅ | CF₃ | H | Q₄ |
| 455 | O | H | CO₂C₂H₅ | CF₃ | CH₃ | Q₄ |
| 456 | O | H | CO₂C₂H₅ | CH₃ | Cl | Q₄ |
| 457 | O | H | SO₂CH₃ | CH₃ | Cl | Q₄ |
| 458 | O | CH₃ | SO₂CH₃ | CF₃ | H | Q₄ |
| 459 | O | H | COPh | CF₃ | CH₃ | Q₄ |
| 460 | O | H | COPh-4-Cl | CH₃ | Cl | Q₄ |
| 461 | O | H | COPh-4-NO₂ | CF₃ | Br | Q₄ |
| 462 | O | H | CONHCOPh | CF₃ | H | Q₄ |
| 463 | O | H | CONHCOPh-2,6-2F | CF₃ | H | Q₄ |
| 464 | O | C₂H₅ | C₂H₅ | CH₃ | H | Q₄ |
| 465 | O | C₂H₅ | C₂H₅ | CF₃ | H | Q₄ |
| 466 | O | C₂H₅ | C₂H₅ | cyclopropyl | H | Q₄ |
| 467 | O | C₂H₅ | C₂H₅ | Ph | H | Q₄ |
| 468 | O | i-Pr | Ph | Ph | H | Q₄ |
| 469 | O | i-Pr | Ph | CH₃ | CH₃ | Q₄ |
| 470 | O | H | NHCH₂CF₃ | CF₃ | H | Q₄ |
| 471 | O | H | OCH₃ | CF₃ | H | Q₄ |
| 472 | O | H | CH₃ | CH₃ | H | Q₅ |
| 473 | O | H | CH₃ | i-Pr | Cl | Q₅ |
| 474 | O | H | Ph | CF₃ | H | Q₅ |
| 475 | O | H | Ph | Br | H | Q₅ |
| 476 | O | H | Ph | OCH₃ | H | Q₅ |
| 477 | O | H | Ph | OCH₂CF₃ | H | Q₅ |
| 478 | O | H | Ph | CF₃ | CH₃ | Q₅ |
| 479 | O | H | Ph | i-Pr | CH₃ | Q₅ |
| 480 | O | H | Ph | t-Bu | Cl | Q₅ |
| 481 | O | H | Ph | cyclopropyl | Cl | Q₅ |
| 482 | O | H | Ph | CF₃ | OCH₃ | Q₅ |
| 483 | O | H | Ph | CF₃ | NHCH₃ | Q₅ |
| 484 | O | H | Ph | CH₃ | SO₂CH₃ | Q₅ |
| 485 | O | H | Ph | CF₃ | Ph-2-CH₃ | Q₅ |
| 486 | O | H | Ph | CF₃ | Ph-4-NO₂ | Q₅ |
| 487 | O | H | Ph | CF₃ | CH₂Ph | Q₅ |
| 488 | O | H | Ph | CF₃ | CH₂Ph-4-Cl | Q₅ |

TABLE 9-continued

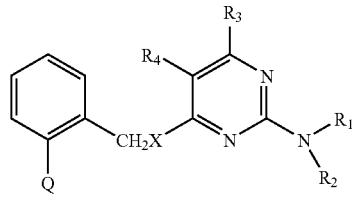

| No. | X | R₁ | R₂ | R₃ | R₄ | Q |
|---|---|---|---|---|---|---|
| 489 | S | H | Ph | CF₃ | H | Q₅ |
| 490 | S | H | Ph | CF₃ | Ph | Q₅ |
| 491 | S | H | Ph | CF₃ | Ph-4-Cl | Q₅ |
| 492 | O | H | COCH₃ | CF₃ | SCH₃ | Q₅ |
| 493 | O | H | COCH₃ | CF₃ | NHCH₃ | Q₅ |
| 494 | O | H | COCH₂Cl | CF₃ | H | Q₅ |
| 495 | O | H | COCH₂Cl | CF₃ | CH₃ | Q₅ |
| 496 | O | H | CO₂C₂H₅ | CF₃ | H | Q₅ |
| 497 | O | H | CO₂C₂H₅ | CF₃ | CH₃ | Q₅ |
| 498 | O | H | SO₂CH₃ | CH₃ | Cl | Q₅ |
| 499 | O | CH₃ | SO₂CH₃ | CF₃ | H | Q₅ |
| 500 | O | H | COPh | CF₃ | CH₃ | Q₅ |
| 501 | O | H | COPh-4-Cl | CH₃ | Cl | Q₅ |
| 502 | O | H | COPh-4-NO₂ | CF₃ | Br | Q₅ |
| 503 | O | C₂H₅ | C₂H₅ | CF₃ | H | Q₅ |
| 504 | O | C₂H₅ | C₂H₅ | cyclopropyl | H | Q₅ |
| 505 | O | i-Pr | Ph | Ph | H | Q₅ |
| 506 | O | i-Pr | Ph | CH₃ | CH₃ | Q₅ |
| 507 | O | H | NHCH₂CF₃ | CF₃ | H | Q₅ |
| 508 | O | H | OCH₃ | CF₃ | H | Q₆ |
| 509 | O | H | CH₃ | CH₃ | H | Q₆ |
| 510 | O | H | CH₃ | i-Pr | Cl | Q₆ |
| 511 | O | H | Ph | CF₃ | H | Q₆ |
| 512 | O | H | Ph | Br | H | Q₆ |
| 513 | O | H | Ph | OCH₃ | H | Q₆ |
| 514 | O | H | Ph | CF₃ | CH₃ | Q₆ |
| 515 | O | H | Ph | cyclopropyl | Cl | Q₆ |
| 516 | O | H | Ph | CF₃ | OCH₃ | Q₆ |
| 517 | S | H | Ph | CF₃ | H | Q₆ |
| 518 | O | H | COCH₃ | CF₃ | SCH₃ | Q₆ |
| 519 | O | H | COCH₂Cl | CF₃ | H | Q₆ |
| 520 | O | H | COCH₂Cl | CF₃ | CH₃ | Q₆ |
| 521 | O | H | SO₂CH₃ | CH₃ | Cl | Q₆ |
| 522 | O | H | COPh | CF₃ | CH₃ | Q₆ |
| 523 | O | H | COPh-4-Cl | CH₃ | Cl | Q₆ |
| 524 | O | C₂H₅ | C₂H₅ | CF₃ | H | Q₆ |
| 525 | O | C₂H₅ | C₂H₅ | cyclopropyl | H | Q₆ |
| 526 | O | i-Pr | Ph | Ph | H | Q₆ |
| 527 | O | i-Pr | Ph | CH₃ | CH₃ | Q₆ |
| 528 | O | H | NHCH₂CF₃ | CF₃ | H | Q₆ |
| 529 | O | H | OCH₃ | CF₃ | H | Q₆ |
| 530 | O | H | OCH₃ | CF₃ | H | Q₆ |
| 531 | O | H | CH₃ | CH₃ | H | Q₆ |
| 532 | O | H | CH₃ | i-Pr | Cl | Q₆ |
| 533 | O | H | Ph | Br | H | Q₆ |
| 534 | O | H | Ph | OCH₃ | H | Q₆ |
| 535 | O | H | Ph | CF₃ | CH₃ | Q₆ |
| 536 | O | H | Ph | i-Pr | CH₃ | Q₆ |
| 537 | O | H | Ph | cyclopropyl | Cl | Q₆ |
| 538 | O | H | Ph | CF₃ | OCH₃ | Q₆ |
| 539 | O | H | Ph | CF₃ | CH₂Ph-4-Cl | Q₆ |
| 540 | O | H | COCH₃ | CF₃ | SCH₃ | Q₆ |
| 541 | O | H | COCH₂Cl | CF₃ | H | Q₆ |
| 542 | O | H | COCH₂Cl | CF₃ | CH₃ | Q₆ |
| 543 | O | H | CO₂C₂H₅ | CF₃ | H | Q₆ |
| 544 | O | H | SO₂CH₃ | CH₃ | Cl | Q₆ |
| 545 | O | H | COPh | CF₃ | CH₃ | Q₆ |
| 546 | O | H | COPh-4-Cl | CH₃ | Cl | Q₆ |
| 547 | O | C₂H₅ | C₂H₅ | CF₃ | H | Q₆ |
| 548 | O | C₂H₅ | C₂H₅ | cyclopropyl | H | Q₆ |
| 549 | O | i-Pr | Ph | CH₃ | CH₃ | Q₆ |
| 550 | O | H | NHCH₂CF₃ | CF₃ | H | Q₆ |
| 551 | O | H | OCH₃ | CF₃ | H | Q₆ |
| 552 | O | H | OCH₃ | CF₃ | H | Q₇ |
| 553 | O | H | CH₃ | CF₃ | H | Q₇ |
| 554 | O | H | CH₃ | i-Pr | Cl | Q₇ |
| 555 | O | H | Ph | CF₃ | H | Q₇ |

TABLE 9-continued

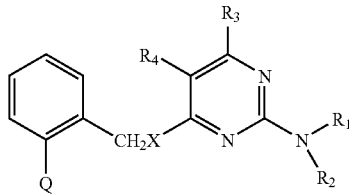

| No. | X | $R_1$ | $R_2$ | $R_3$ | $R_4$ | Q |
|---|---|---|---|---|---|---|
| 556 | O | H | Ph | Br | H | $Q_7$ |
| 557 | O | H | Ph | $OCH_3$ | H | $Q_7$ |
| 558 | O | H | Ph | $CF_3$ | $CH_3$ | $Q_7$ |
| 559 | O | H | Ph | cyclopropyl | Cl | $Q_7$ |
| 560 | O | H | $SO_2CH_3$ | $CH_3$ | Cl | $Q_7$ |
| 561 | O | H | COPh | $CF_3$ | $CH_3$ | $Q_7$ |
| 562 | O | H | COPh-4-Cl | $CH_3$ | Cl | $Q_7$ |
| 563 | O | $C_2H_5$ | $C_2H_5$ | $CF_3$ | H | $Q_7$ |
| 564 | O | i-Pr | Ph | Ph | H | $Q_7$ |
| 565 | O | i-Pr | Ph | $CH_3$ | $CH_3$ | $Q_7$ |
| 566 | O | H | $NHCH_2CF_3$ | $CF_3$ | H | $Q_7$ |
| 567 | O | H | $OCH_3$ | $CF_3$ | H | $Q_7$ |
| 568 | O | H | $CH_3$ | $CH_3$ | H | $Q_7$ |
| 569 | O | H | $CH_3$ | i-Pr | Cl | $Q_7$ |
| 570 | O | H | Ph | i-Pr | $CH_3$ | $Q_7$ |
| 571 | O | H | Ph | cyclopropyl | Cl | $Q_7$ |
| 572 | O | H | $COCH_3$ | $CF_3$ | $SCH_3$ | $Q_7$ |
| 573 | O | H | $COCH_2Cl$ | $CF_3$ | H | $Q_7$ |
| 574 | O | H | $SO_2CH_3$ | $CH_3$ | Cl | $Q_7$ |
| 575 | O | H | COPh | $CF_3$ | $CH_3$ | $Q_7$ |
| 576 | O | H | COPh-4-Cl | $CH_3$ | Cl | $Q_7$ |
| 577 | O | $C_2H_5$ | $C_2H_5$ | $CF_3$ | H | $Q_7$ |
| 578 | O | i-Pr | Ph | $CH_3$ | $CH_3$ | $Q_7$ |
| 579 | O | H | $OCH_3$ | $CF_3$ | H | $Q_7$ |
| 580 | O | H | $OCH_3$ | $CF_3$ | H | $Q_8$ |
| 581 | O | H | $CH_3$ | $CF_3$ | H | $Q_8$ |
| 582 | O | H | Ph | $CF_3$ | H | $Q_8$ |
| 583 | O | H | Ph | Br | H | $Q_8$ |
| 584 | O | H | Ph | cyclopropyl | Cl | $Q_8$ |
| 585 | O | H | $SO_2CH_3$ | $CH_3$ | Cl | $Q_8$ |
| 586 | O | H | COPh | $CF_3$ | $CH_3$ | $Q_8$ |
| 587 | O | H | COPh-4-Cl | $CH_3$ | Cl | $Q_8$ |
| 588 | O | $C_2H_5$ | $C_2H_5$ | $CF_3$ | H | $Q_8$ |
| 589 | O | i-Pr | Ph | Ph | H | $Q_8$ |
| 590 | O | i-Pr | Ph | $CH_3$ | $CH_3$ | $Q_8$ |
| 591 | O | H | $NHCH_2CF_3$ | $CF_3$ | H | $Q_8$ |
| 592 | O | H | $OCH_3$ | $CF_3$ | H | $Q_8$ |
| 593 | O | H | $CH_3$ | i-Pr | Cl | $Q_8$ |
| 594 | O | H | Ph | i-Pr | $CH_3$ | $Q_8$ |
| 595 | O | H | Ph | cyclopropyl | Cl | $Q_8$ |
| 596 | O | H | $COCH_3$ | $CF_3$ | $SCH_3$ | $Q_8$ |
| 597 | O | H | COPh-4-Cl | $CH_3$ | Cl | $Q_8$ |
| 598 | O | H | $OCH_3$ | $CF_3$ | H | $Q_8$ |
| 599 | O | H | $CH_3$ | $CF_3$ | H | $Q_9$ |
| 600 | O | H | Ph | $CF_3$ | H | $Q_9$ |
| 601 | O | H | Ph | Br | H | $Q_9$ |
| 602 | O | H | $SO_2CH_3$ | $CH_3$ | Cl | $Q_9$ |
| 603 | O | H | COPh | $CF_3$ | $CH_3$ | $Q_9$ |
| 604 | O | H | COPh-4-Cl | $CH_3$ | Cl | $Q_9$ |
| 605 | O | $C_2H_5$ | $C_2H_5$ | $CF_3$ | H | $Q_9$ |
| 606 | O | i-Pr | Ph | $CH_3$ | $CH_3$ | $Q_9$ |
| 607 | O | H | $NHCH_2CF_3$ | $CF_3$ | H | $Q_9$ |
| 608 | O | H | $CH_3$ | i-Pr | Cl | $Q_9$ |
| 609 | O | H | Ph | i-Pr | $CH_3$ | $Q_9$ |
| 610 | O | H | Ph | cyclopropyl | Cl | $Q_9$ |
| 611 | O | H | COPh-4-Cl | $CH_3$ | Cl | $Q_9$ |
| 612 | O | H | $OCH_3$ | $CF_3$ | H | $Q_9$ |
| 613 | O | H | $CH_3$ | $CF_3$ | H | $Q_{10}$ |
| 614 | O | H | Ph | $CF_3$ | H | $Q_{10}$ |
| 615 | O | H | Ph | Br | H | $Q_{10}$ |
| 616 | O | H | COPh-4-Cl | $CH_3$ | Cl | $Q_{10}$ |
| 617 | O | $C_2H_5$ | $C_2H_5$ | $CF_3$ | H | $Q_{10}$ |
| 618 | O | i-Pr | Ph | $CH_3$ | $CH_3$ | $Q_{10}$ |
| 619 | O | H | $NHCH_2CF_3$ | $CF_3$ | H | $Q_{10}$ |
| 620 | O | H | $CH_3$ | i-Pr | Cl | $Q_{10}$ |
| 621 | O | H | Ph | cyclopropyl | Cl | $Q_{10}$ |
| 622 | O | H | COPh-4-Cl | $CH_3$ | Cl | $Q_{10}$ |

TABLE 9-continued

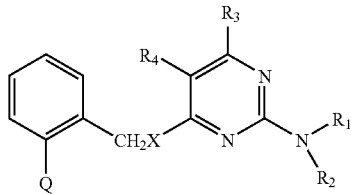

I

| No. | X | R₁ | R₂ | R₃ | R₄ | Q |
|---|---|---|---|---|---|---|
| 623 | O | H | OCH₃ | CF₃ | H | Q₁₀ |
| 624 | O | H | CH₃ | CF₃ | H | Q₁₁ |
| 625 | O | H | Ph | CF₃ | H | Q₁₁ |
| 626 | O | H | Ph | Br | H | Q₁₁ |
| 627 | O | H | COPh-4-Cl | CH₃ | Cl | Q₁₁ |
| 628 | O | C₂H₅ | C₂H₅ | CF₃ | H | Q₁₁ |
| 629 | O | i-Pr | Ph | CH₃ | CH₃ | Q₁₁ |
| 630 | O | H | NHCH₂CF₃ | CF₃ | H | Q₁₁ |
| 631 | O | H | CH₃ | i-Pr | Cl | Q₁₁ |
| 632 | O | H | Ph | cyclopropyl | Cl | Q₁₁ |
| 633 | O | H | OCH₃ | CF₃ | H | Q₁₁ |
| 634 | O | H | CH₃ | CF₃ | H | Q₁₂ |
| 635 | O | H | Ph | CF₃ | H | Q₁₂ |
| 636 | O | H | Ph | Br | H | Q₁₂ |
| 637 | O | H | COPh-4-Cl | CH₃ | Cl | Q₁₂ |
| 638 | O | C₂H₅ | C₂H₅ | CF₃ | H | Q₁₂ |
| 639 | O | i-Pr | Ph | CH₃ | CH₃ | Q₁₂ |
| 640 | O | H | NHCH₂CF₃ | CF₃ | H | Q₁₂ |
| 641 | O | H | CH₃ | i-Pr | Cl | Q₁₂ |
| 642 | O | H | Ph | cyclopropyl | Cl | Q₁₂ |
| 643 | O | H | OCH₃ | CF₃ | H | Q₁₂ |
| 644 | O | H | CH₃ | CF₃ | H | Q₁₃ |
| 645 | O | H | Ph | CF₃ | H | Q₁₃ |
| 646 | O | H | Ph | Br | H | Q₁₃ |
| 647 | O | H | COPh-4-Cl | CH₃ | Cl | Q₁₃ |
| 648 | O | C₂H₅ | C₂H₅ | CF₃ | H | Q₁₃ |
| 649 | O | i-Pr | Ph | CH₃ | CH₃ | Q₁₃ |
| 650 | O | H | NHCH₂CF₃ | CF₃ | H | Q₁₃ |
| 651 | O | H | CH₃ | i-Pr | Cl | Q₁₃ |
| 652 | O | H | Ph | cyclopropyl | Cl | Q₁₃ |
| 653 | O | H | OCH₃ | CF₃ | H | Q₁₃ |
| 654 | O | H | CH₃ | CF₃ | H | Q₁₄ |
| 655 | O | H | Ph | CF₃ | H | Q₁₄ |
| 656 | O | H | Ph | Br | H | Q₁₄ |
| 657 | O | H | C₃H₇-i | CF₃ | H | Q₁₄ |
| 658 | O | H | NHCH₂CF₃ | CF₃ | H | Q₁₄ |
| 659 | O | H | Ph-2-Cl | CH₃ | Cl | Q₁ |
| 660 | O | H | Ph-2-CH₃ | CF₃ | H | Q₁ |
| 661 | O | H | Ph-3,5-2Cl | CF₃ | H | Q₁ |
| 662 | O | H | Ph-2-CH₃-3-Cl | CF₃ | H | Q₁ |
| 663 | O | H | C(CH₃)₃ | CF₃ | H | Q₁ |
| 664 | O | H | Ph | cyclopropyl | H | Q₄ |
| 665 | O | H | Ph | cyclopropyl | H | Q₃ |
| 666 | O | H | Ph | cyclopropyl | H | Q₅ |
| 667 | O | H | Ph | CH₃ | CH₃ | Q₂ |
| 668 | O | H | Ph | CH₃ | CH₃ | Q₄ |
| 669 | O | H | Ph | CH₃ | CH₃ | Q₃ |
| 670 | O | H | Ph | CH₃ | CH₃ | Q₅ |
| 671 | O | H | Ph | CH₃ | (CH₂)₃CH₃ | Q₁ |
| 672 | O | H | Ph | CH₃ | (CH₂)₃CH₃ | Q₂ |
| 673 | O | H | Ph | CH₃ | (CH₂)₃CH₃ | Q₄ |
| 674 | O | H | Ph | CH₃ | (CH₂)₃CH₃ | Q₃ |
| 675 | O | H | Ph | CH₃ | (CH₂)₃CH₃ | Q₅ |
| 676 | O | H | Ph | CH₃ | H | Q₂ |
| 677 | O | H | Ph | CH₃ | H | Q₄ |
| 678 | O | H | Ph | CH₃ | H | Q₃ |
| 679 | O | H | Ph | CH₃ | H | Q₅ |
| 680 | O | CH₃ | CH₃ | CF₃ | H | Q₁ |
| 681 | O | H | 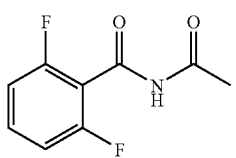 | CF₃ | H | Q₁ |

TABLE 9-continued

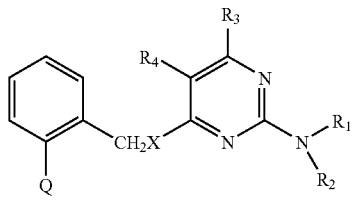

I

| No. | X | R₁ | R₂ | R₃ | R₄ | Q |
|---|---|---|---|---|---|---|
| 682 | O | H | CH(CH₃)₂ | CF₃ | H | Q₁ |
| 683 | O | CH₃ | NH₂ | CF₃ | H | Q₁ |
| 684 | O | H | Ph-4-CF₃ | CF₃ | H | Q₁ |
| 685 | O | H | Ph-2,6-2F | CF₃ | H | Q₁ |
| 686 | O | H | Ph-2,6-2Cl | CF₃ | H | Q₁ |
| 687 | O | H | Ph-3-Cl | CF₃ | H | Q₁ |
| 688 | O | H | Ph-4-OCH₃ | CF₃ | H | Q₁ |
| 689 | O | H | Ph-4-F | CF₃ | H | Q₁ |
| 690 | O | H | Ph-4-CH₃ | CF₃ | H | Q₁ |
| 691 | O | H | 2-chloro-pyridin-3-yl | CF₃ | H | Q₁ |
| 692 | O | H | cyclopropyl | CF₃ | H | Q₁ |
| 693 | O | H | Ph-2,4-2CH₃ | CF₃ | H | Q₁ |
| 694 | O | H | Ph2,3-2Cl | CF₃ | H | Q₁ |
| 695 | O | H | Ph-2,5-2CH₃ | CF₃ | H | Q₁ |
| 696 | O | H | CH₂Ph-2-Cl | CF₃ | H | Q₁ |
| 697 | O | H | Ph-3,4-2CH₃ | CF₃ | H | Q₁ |
| 698 | O | H | Ph-2,4,5-3CH₃ | CF₃ | H | Q₁ |
| 699 | O | H | Ph-2-CH₃-4-Cl | CF₃ | H | Q₁ |
| 700 | O | H | CH₂Ph | CF₃ | H | Q₁ |
| 701 | O | H | cyclohexanyl | CF₃ | H | Q₁ |
| 702 | O | H | C₂H₅ | CF₃ | H | Q₁ |
| 703 | O | H | Ph-4-Cl | CH₃ | H | Q₁ |
| 704 | O | H | Ph-4-Cl | CF₃ | H | Q₁ |
| 705 | O | H | (CH₂)₃CH₃ | CF₃ | H | Q₁ |
| 706 | O | H | CH₂CH(CH₃)₂ | CF₃ | H | Q₁ |
| 707 | O | H | CH(CH₃)CH₂CH₃ | CF₃ | H | Q₁ |
| 708 | O | H | CH₂C(CH₃)₃ | CF₃ | H | Q₁ |
| 709 | O |  | | CF₃ | H | Q₁ |
| 710 | O | 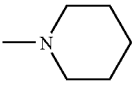 | | CF₃ | H | Q₁ |
| 711 | O | 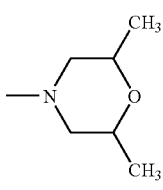 | | CF₃ | H | Q₁ |
| 712 | O | 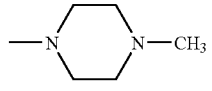 | | CF₃ | H | Q₁ |
| 713 | O | 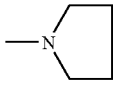 | | CF₃ | H | Q₁ |
| 714 | O | 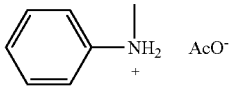 | | CF₃ | H | Q₁ |

TABLE 9-continued

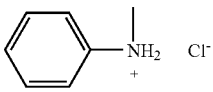

| No. | X | R₁ | R₂ | R₃ | R₄ | Q |
|---|---|---|---|---|---|---|
| 715 | O | | phenyl-NH₂⁺ Cl⁻ | CF₃ | H | Q₁ |
| 716 | O | | (H₃C)₂CH-NH₂⁺ , phenyl-SO₃⁻ | CF₃ | H | Q₁ |
| 717 | O | | (H₃C)₂CH-NH₂⁺ , CO₂H-CO₂⁻ | CF₃ | H | Q₁ |
| 718 | O | | (H₃C)(H₃C-CH₂)CH-NH₂⁺ , CO₂H-CO₂⁻ | CF₃ | H | Q₁ |

The present invention also includes preparation of the compounds having formula I:

When Q is chosen from one of $Q_1$, $Q_2$, $Q_4$, $Q_6$-$Q_{13}$, compounds having general formula I and their stereoisomers can be prepared by reaction of pyrimidine compounds containing hydroxy group having general formula III with halomethylbenzene having general formula IV at the present of base:

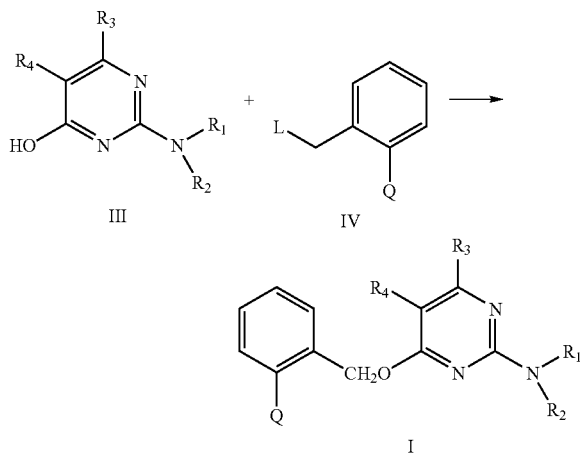

Wherein: L is leaving group, such as Cl or Br, other groups are as defined above. Intermediate of the general IV can be prepared according to known methods, refer to U.S. Pat. No. 4,723,034 and U.S. Pat. No. 5,554,578.

The reaction can be carried out in proper solvent, which may be selected from tetrahydrofuran, acetonitrile, toluene, xylene, benzene, DMF, DMSO, acetone or butanone and so on.

The proper base mentioned above may be selected from potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide and so on.

The proper temperature mentioned above is from room temperature to boiling point of solvent, normal temperature is from 20 to 100° C.

The reaction may be finished after 30 minutes to 20 hours, 1 hour to 10 hours in general.

The compounds having general formula I wherein Q represents $Q_3$, $Q_5$ or $Q_{14}$ can be prepared by reaction of the corresponding compounds wherein Q is selected from $Q_2$, $Q_4$ or $Q_{12}$ with methylamine aqueous.

Suitable salts of formula I were obtained from the compounds of formula I with 2-aminopyrimidine group reacting with inorganic acids, for example hydrochloride, phosphates and organic acids such as acetic acid, benzenesulfonic acid, oxalic acid.

Intermediate of the general formula III can be prepared by reaction of intermediate of the general formula II with ethyl 3-oxobutanoate, ethyl 4,4,4-trifluoro-3-oxobutanoate according to known methods, refer to GB1388402, U.S. Pat. No. 4,000,138, $CH_{395385}$. Intermediate of the general formula II can be bought or prepared according to known methods, refer to EP310550, EP0655441.

Part of intermediates III are listed in table 10:

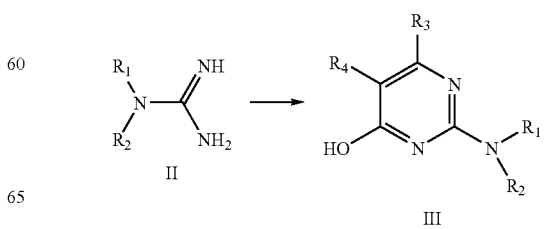

TABLE 10

Intermediate III

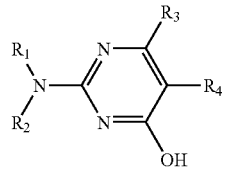

| No. | R₁ | R₂ | R₃ | R₄ | m.p. (□) |
|---|---|---|---|---|---|
| 1 | H | H | CF₃ | H | 276-278 |
| 2 | H | Ph | CH₃ | H | 258-260 |
| 3 | H | Ph | CF₃ | H | 279-281 |
| 4 | H | Ph | CH₃ | CH₃ | 282-284 |
| 5 | H | Ph | CH₃ | (CH₂)₃CH₃ | 183-185 |
| 6 | H | Ph | cyclopropyl | H | 112-115 |
| 7 | H | Ph | 2-chloro-pyridin-5-yl | H | 204-205 |
| 8 | H | Ph | 2-(2,2,2-trifluoroethoxy)pyridin-5-yl | H | 227-228 |
| 9 | H | Ph-4-Cl | CH₃ | H | 251-253 |
| 10 | H | Ph-4-Cl | CF₃ | H | 276-278 |
| 11 | H | Ph-4-Cl | CF₃ | Cl | |
| 12 | H | NH₂ | CF₃ | H | 228-230 |
| 13 | CH₃ | CH₃ | CF₃ | H | 174-176 |
| 14 | CH₂CH₃ | CH₂CH₃ | CF₃ | H | 111-112 |
| 15 | H | CH(CH₃)₂ | CF₃ | H | 176-178 |
| 16 | CH₃ | NH₂ | CF₃ | H | 183-185 |
| 17 | H | Ph-4-CF₃ | CF₃ | H | 213-215 |
| 18 | H | Ph-2,6-2F | CF₃ | H | 158-160 |
| 19 | H | Ph-2,6-2Cl | CF₃ | H | 216-218 |
| 20 | H | Ph-3-Cl | CF₃ | H | 196-198 |
| 21 | H | Ph-4-OCH₃ | CF₃ | H | 156-158 |
| 22 | H | Ph-4-CH₃ | CF₃ | H | 207-209 |
| 23 | H | Ph-4-F | CF₃ | H | 204-206 |
| 24 | H | 2-chloro-pyridin-3-yl | CF₃ | H | >295 |
| 25 | H | cyclopropyl | CF₃ | H | 181-183 |
| 26 | H | Ph-2-CH₃ | CF₃ | H | 222-224 |
| 27 | H | Ph-2-Cl | CF₃ | H | >290 |
| 28 | H | Ph-2-CH₃-3-Cl | CF₃ | H | 234-236 |
| 29 | H | Ph-2,4-2CH₃ | CF₃ | H | 230-232 |
| 30 | H | Ph-2,3-2Cl | CF₃ | H | 264-266 |
| 31 | H | Ph-3,5-2Cl | CF₃ | H | 287-288 |
| 32 | H | Ph-2,5-2CH₃ | CF₃ | H | 216-218 |
| 33 | H | CH₂Ph-2-Cl | CF₃ | H | 157-159 |
| 34 | H | Ph-3,4-2CH₃ | CF₃ | H | 136-137 |
| 35 | H | Ph-2,4,5-3Cl | CF₃ | H | 260-262 |
| 36 | H | Ph-2-CH₃-4-Cl | CF₃ | H | 212-214 |
| 37 | H | CH₂Ph | CF₃ | H | 152-154 |
| 38 | H | cyclohexanyl | CF₃ | H | 234-235 |
| 39 | H | CH₃ | CF₃ | H | 244-247 |
| 40 | H | CH₂CH₃ | CF₃ | H | 192-194 |
| 41 | H | CH₂CH(CH₃)₂ | CF₃ | H | |
| 42 | H | CH(CH₃)CH₂CH₃ | CF₃ | H | |
| 43 | C₄H₉-n | C₄H₉-n | CF₃ | H | |
| 44 | H | CH₂CH₂CH₃ | CF₃ | H | |
| 45 | H | cyclopentanyl | CF₃ | H | 168-170 |
| 46 | H | benzothiazol-2-yl | CF₃ | H | |
| 47 | H | thiazol-2-yl | CF₃ | H | |
| 48 | H | CH₂(CH₂)₂CH₃ | CF₃ | H | 152-154 |
| 49 | H | CH₂C(CH₃)₃ | CF₃ | H | 172-174 |
| 50 | H | C(CH₃)₃ | CF₃ | H | 88-90 |
| 51 | H | N(CH₃)₂ | CF₃ | H | 179-180 |
| 52 | H | OCH₃ | CF₃ | H | 162-164 |
| 53 | H | OCH₂CH₃ | CF₃ | H | 166-168 |
| 54 | H | CH(CN)CH₃ | CF₃ | H | |
| 55 | H | C(CN)(CH₃)₂ | CF₃ | H | |
| 56 | H | CN | CF₃ | H | 164-166 |
| 57 | H | CH₂CN | CF₃ | H | |
| 58 | H | CH₂CH₂CN | CF₃ | H | |
| 59 | H | N=C(CH₃)₂ | CF₃ | H | |

TABLE 10-continued

Intermediate III

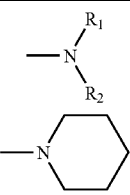

| No. | R₁ | R₂ | R₃ | R₄ | m.p. (□) |
|---|---|---|---|---|---|
| 60 | | piperidine (R₁,R₂ joined) | $CF_3$ | H | 168-170 |
| 61 | | morpholine | $CF_3$ | H | 261-263 |
| 62 | | 2,6-dimethylmorpholine | $CF_3$ | H | 220-222 |

| Intremediate No. | ¹H-NMR (300 MHz, internal standard TMS, solvent CDCl₃) |
|---|---|
| 13 | δ (ppm): 3.01 (s, 6H), 5.94 (s, 1H). |
| 14 | δ (ppm): 1.22 (t, 6H), 3.59 (q, 4H), 6.03 (s, 1H). |
| 15 | δ (ppm): 1.27 (d, 6H), 4.19 (m, 1H), 6.02 (s, 1H). |
| 16 | δ (ppm): 3.43 (s, 3H), 6.12 (s, 1H). |
| 17 | δ (ppm): 5.11 (s, 1H), 6.42 (s, 1H), 7.50 (m, 1H), 7.65 (m, 1H), 7.76 (m, 1H), 7.91 (m, 1H) (solvent DMSO). |

The compounds having general formula I, which is exerted with respect to the adults, larvae and eggs of mites and insects which are harmful in the agricultural, have a high acaricidal and insecticidal activity, while the compounds also exhibit preferably fungicidal activity.

A further object of the present invention therefore relates to the use of the compounds having general formula I as acaricides, insecticides, and fungicides, both in agriculture and other fields. In particular, the compounds having general formula I are active against important species of tetranychidae (*Tetranychus urticae, Tetranychus cinnabarinus, Panonychus ulmi, Panonychus citri,* etc.), eriophyidae, tarsonemidae, etc. Additionally, some compounds in present invention also exhibit good fungicidal activity, which can be used to control of rice blast, tomato late blight, cucumber downy mildew, cucumber anthracnose, corn rust, wheat powdery mildew etc.

At the same time, the compounds having general formula I have a low toxicity with respect to many useful insects and mites, mammals, fish, birds, and have no phytotoxicity.

Thanks to their positive characteristics, they can be advantageously used in defending not only crops of agrarian and horticultural interest, but also domestic and breeding animals, as well as environments frequented by human beings, from harmful mites and insects.

For obtaining the desired effect, the quality of compounds can be varied in relation to various factors such as, the compound used, the crop to be preserved, the type of harmful organism, the degree of infestation, the climatic conditions, the method of application, the formulation adopted.

Doses of compounds ranging from 10 g to 5 kg per hectare generally provide a sufficient control.

A further object of the present invention also relates to a method for controlling mites and/or insects and/or phytopathogenic fungi in crops of agrarian and horticultural interest and/or on domestic and breeding animals and/or environments frequented by human beings, by the application of the compounds having general formula I. In particular, the quantity of compounds to be applied varies from 10 g to 5 kg per hectare.

For practical application in agriculture, it is usually beneficial to use compositions containing one or more compounds having general formula I.

A further object of the present invention therefore relates to acaricidal, insecticidal and fungicidal compositions containing compounds having general formula I as active principle and acceptable carrier in agriculture, the active component of the compositions is 0.5-90%.

Compositions can be used in the form of dry powders, wettable powders, emulsifiable concentrates, microemulsions, pastes, granulates, solutions, suspensions, etc.: the selection of the type of compositions depends on the specific application.

The compositions are prepared in the known way, for example by diluting or dissolving the active substance with a solvent medium and/or a solid diluent, optionally in the presence of surfactant Solid diluents, or carriers which can be used are, for example: silica, kaolin, bentonite, talc, diatomite, dolomite, calcium carbonate, magnesia, chalk, clays, synthetic silicates, attapulgite, sepiolite.

Liquid diluents which can be used are, for example, besides water, aromatic organic solvents (xylols or mixtures of alkylbenzols, chlorobenzene, etc.), paraffins (petroleum fractions), alcohols (methanol, propanol, butanol, octanol, glycerin, etc.), esters (ethyl acetate, isobutyl acetate, etc.), ketones (cyclohexanone, acetone, acetophenone, isophorone, ethylamylketone, etc.), amides (N, N-dimethylformamide, N-methylpyrrolidone, etc.).

Surfactant which can be used are salts of sodium, calcium, triethylamine or triethanolamine of alkylsulfonates, alkylarylsulfonates, polyethoxylated alkylphenols, polyethoxylated esters of sorbitol, ligninsulfonates, etc.

The compositions can also contain special additives for particular purposes, for example adhesive such as Arabic gum, polyvinyl alcohol, polyvinyl-pyrrolidone, etc.

The concentration of active principle in the above compositions can vary within a wide range depending on the active compound, the applications for which they are destined, the environmental conditions and the type of formulation adopted. In general the concentration of active principle ranges from 1 to 90%, preferably from 5 to 50%.

It is possible to add to the compositions, other active principles compatible with the compounds having general formula I according to requirement, such as, for example, other acaricides/insecticides, fungicides, phytoregulators, antibiotics, herbicides, fertilizers.

Several formulations of preparation methods, for example as follows:

The preparation of suspension concentrate: the common active component in formula is 5% -35%. With water as the medium, the compound, dispersing agent, suspending agent and antifreeze agent are added to sanding machine for grinding to make suspension concentrate.

The preparation of water emulsion: the compound, solvent and emulsifier are mixed together, to make a homogeneous oil phase. The water is mixed with antifreeze, as a homogeneous water phase. In the high-speed stirring, the aqueous phase added to the oil phase or oil phase is added to the aqueous phase, forming a good dispersion of the water emulsion. The active component of emulsions is generally 5%-15% in this invention. For the production of concentrated emulsions, the compounds of this invention are soluble in one or more of the mixed solvent, and then emulsifier is added to enhance dispersion effects in the water.

The preparation of wettable powder: the compound, surfactants and solid diluent are mixed well according to recipe requirements, after smashing through ultrafine pulverizer, that is the wettable powder products (for example, 10%-40%). For preparing the spraying wettable powder, the compounds of this invention can be mixed with solid power to form the mixture, such as clay, inorganic silicates, carbonates, as well as wetting agents, adhesives and/or dispersant agent.

The preparation of water dispersible granules: the compound and powdered solid diluents, wetting agents and adhesives are mixed to smash, kneaded together with water and added to the granulation 10-100 mesh machine for granulation, then by drying and sieving (at the scope screen). Also, the compounds, dispersants, wetting agents, disintegrants and solid diluent are added sanding machine, grinded with water for medium to produce suspension and then spray-drying granulation, usually the preparation of content is 20%-30% granular products.

DETAILED DESCRIPTION OF THE INVENTION

The following examples are illustrative of the present invention, but without being restricted thereby.

PREPARATION EXAMPLE

Example 1

The preparation of compound 20

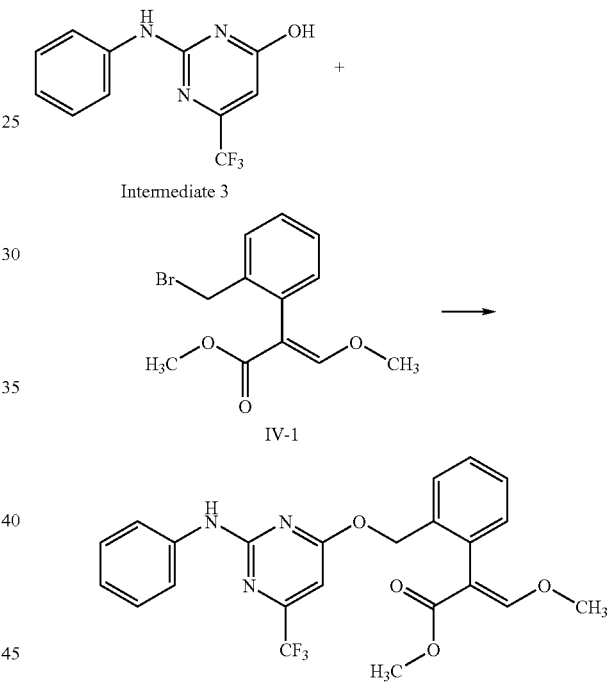

1.32 g of intermediate 3 (prepared according to Bioorganic & Medicinal Chemistry Letters, 2004, 14(17): 4449-4452) was dissolved in 30 ml of butanone, 1.6 g potassium carbonate was added to the solution, which is stirred to no bubble, then 1.25 g intermediate IV-1 was added, heated to reflux, after 8 hours, the reaction was traced by Thin-Layer Chromatography, then the salt was removed by filtration, washed by ethyl acetate, the combined organic exacts were concentrated at reduced pressure. The crude product was purified through silica column (ethyl acetate/petroleum ether (boiling point range 60-90° C.)=1/5, as an eluent) and light yellow thick oil (compound 20) was obtained, which solidified to give 1.52 g product, m.p. 106-109° C.

$^1$H-NMR spectrum (300 MHz, internal standard: TMS, solvent CDCl$_3$) is as follows: δ(ppm): 3.70(s, 3H), 3.78(s, 3H), 5.33(s, 2H), 6.48 (s, 1H), 7.07(m, 1H), 7.20(m, 1H), 7.34(m, 4H), 7.49(m, 2H), 7.58(s, 1H), 7.63(m, 2H).

Example 2

The preparation of compound 680

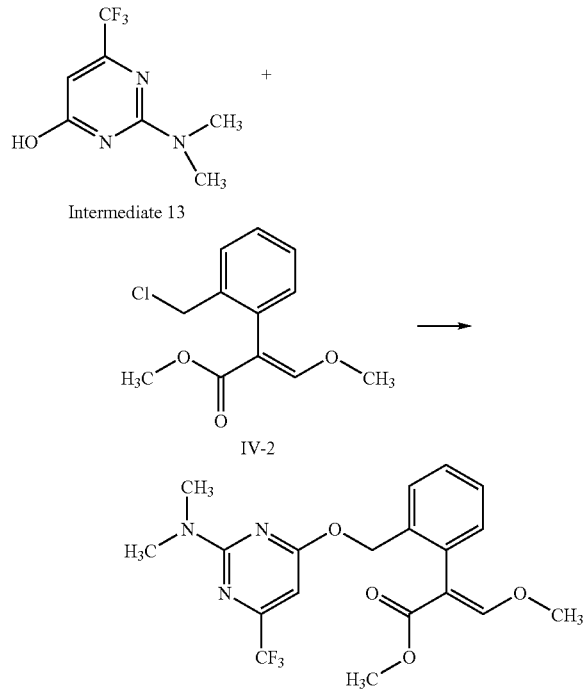

0.50 g intermediate 13 was dissolved in 10 ml DMF, 0.67 g potassium carbonate was added to the solution, which is stirred at room temperature for half an hour, 0.53 g intermediate IV-2 was added, the reaction temperature was rised to 80°. 8 hours later, the reaction was traced by Thin-Layer Chromatography, after the reaction, the reaction mixture was poured into 30 ml saturated brine, extracted with ethyl acetate, the combined organic extracts were dried with sodium sulfate, and concentrated at reduced pressure. The crude product was purified through silica column (ethyl acetate/petroleum ether (boiling point range 60-90° C.)=1/5, as an eluent) and light yellow thick oil (compound 680) was obtained, which solidified to give 0.31 g product, m.p 86-88° C.

$^1$H-NMR spectrum (300 MHz, internal standard:TMS, solvent CDCl$_3$) is as follows: δ(ppm): 3.16(s, 6H), 3.67(s, 3H), 3.80(s, 3H), 5.30(s, 2H), 6.21(s, 1H), 7.20(m, 1H), 7.35(m, 2H), 7.47(m, 1H), 7.57(s, 1H).

Example 3

The preparation of compound 351

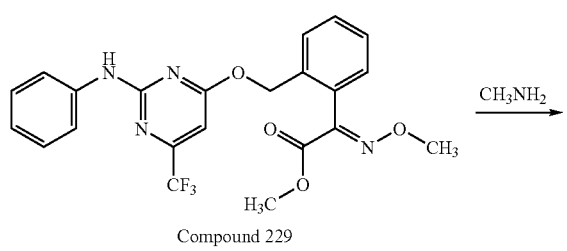

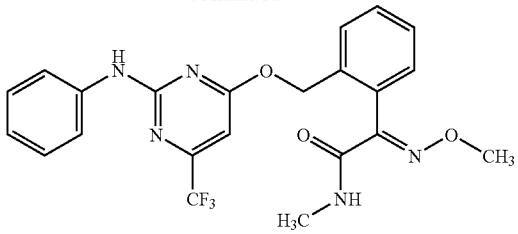

0.32 g compound 229 (the preparation is same with compound 20) was dissolved in 10 ml methanol, 2 ml 30% aqueous solution of methylamine was added, stirred at room temperature for 6 hours, the reaction was traced by Thin-Layer Chromatography, after the reaction, removed solvent at reduced pressure, the crude product was purified through silica gel column(ethyl acetate/petroleum ether (boiling point range 60-90° C.)=1/3, as an eluent) and light yellow thick oil (compound 351) was obtained, which solidified to give 0.13 g product, m.p. 119-121° C.

$^1$H-NMR (300 MHz, internal standard:TMS, solvent CDCl$_3$) is as follows: δ(ppm): 2.98 (d, 3H), 3.96(s, 3H), 5.17(s, 2H), 6.46(s, 1H), 7.02(m, 2H), 7.38(m, 5H), 7.73(m, 2H), 8.22(s, 1H).

Other compounds were prepared according the above examples.

Physical and chemical property and $^1$HNMR spectrum ($^1$HNMR, 300 MHz, internal standard:TMS, solvent CDCl$_3$) of some compounds having the general formula I of this invention are as follows:

Compound 2: thick oil. δ(ppm): 2.98(d, 3H), 3.69(s, 3H), 3.81(s, 3H), 5.28(s, 2H), 6.28(s, 1H), 7.19(m, 1H), 7.34(m, 2H), 7.49(m, 1H), 7.58(s, 1H).

Compound 19: thick oil. δ(ppm): 2.20 (3H, s), 3.71(3H, s), 3.77(3H, s), 5.33(2H, s), 6.52(1H, s), 7.11(1H, m), 7.20(1H, m), 7.39(4H, m), 7.45(2H, m), 7.59(1H, s), 7.60(2H, m).

Compound 22: thick oil. δ(ppm): 3.70(s, 3H), 3.82(s, 3H), 5.25(s, 2H), 5.36(s, 2H), 6.37(s, 1H), 7.17(m, 1H), 7.34(m, 2H), 7.48(m, 1H), 7.59(s, 1H).

Compound 25: m.p. 54-56° C. δ(ppm): 1.01(m, 2H), 1.15 (m, 2H), 1.83(m, 1H), 3.65(s, 3H), 3.78(s, 3H), 5.27(s, 2H), 6.06(s, 1H), 7.01(m, 1H), 7.18(m, 1H), 7.33(m, 4H), 7.51(m, 1H), 7.57(m, 1H), 7.62(m, 2H).

Compound 41: m.p. 136-138° C. δ(ppm): 2.05(s, 3H), 2.36(s, 3H), 3.68(s, 3H), 3.74(s, 3H), 5.32(s, 2H), 6.98(m, 1H), 7.20(m, 1H), 7.35(m, 4H), 7.58(m, 1H), 7.61(s, 1H), 7.63(m, 2H).

Compound 48: thick oil. δ(ppm): 3.74(s, 3H), 3.84(s, 3H), 4.49(s, 2H), 7.13(m, 1H), 7.33(m, 5H), 7.54(m, 2H), 7.60(m, 1H), 7.71(m, 1H).

Compound 109: m.p. 84-85° C. δ(ppm): 1.16(t, 6H), 3.58 (q, 4H), 3.68(s, 3H), 3.80(s, 3H), 5.28(s, 2H), 6.21(s, 1H), 7.18(m, 1H), 7.34(m, 2H), 7.48(m, 1H), 7.57(s, 1H).

Compound 124: thick oil. δ(ppm): 0.97 (t, 3H), 1.61 (m, 2H), 3.36 (m, 2H), 3.69 (s, 3H), 3.80 (s, 3H), 4.30 (m, 1H), 5.29 (s, 2H), 6.27 (s, 1H), 7.17-7.20 (m, 1H), 7.33-7.36 (m, 2H), 7.48-7.51 (m, 1H), 7.58 (s, 1H).

Compound 125: thick oil. δ(ppm): 1.40-1.50 (m, 4H), 1.58-1.74 (m, 4H), 3.69 (s, 3H), 3.81 (s, 3H), 4.30-4.42 (m, 1H), 5.38 (s, 2H), 6.14 (s, 1H), 7.18-7.21 (m, 1H), 7.31-7.36 (m, 2H), 7.48-7.52 (m, 1H), 7.63 (s, 1H).

Compound 126: thick oil.

Compound 127: thick oil.

Compound 171: m.p. 82-84° C. δ(ppm): 0.96 (s, 9H), 3.26 (d, 2H), 3.69 (s, 3H), 3.80 (s, 3H), 5.30 (s, 2H), 6.26 (s, 1H), 7.17-7.20 (m, 1H), 7.33-7.38 (m, 2H), 7.48-7.51 (m, 1H), 7.58 (m, 1H).

Compound 211: m.p. 66-68° C.δ(ppm): 3.54 (s, 3H), 3.60 (s, 3H), 3.74 (s, 3H), 4.07 (m, 2H), 5.30 (s, 2H), 6.40 (s, 1H), 7.15-7.18 (m, 1H), 7.29-7.34 (m, 2H), 7.41-7.44 (m, 1H), 7.53 (s, 1H).

Compound 212: thick oil. δ(ppm): 0.96 (s, 9H), 3.26 (d, 2H), 3.69 (s, 3H), 3.80 (s, 3H), 5.30 (s, 2H), 6.26 (s, 1H), 7.17-7.20 (m, 1H), 7.33-7.38 (m, 2H), 7.48-7.51 (m, 1H), 7.58 (m, 1H).

Compound 216: thick oil. δ(ppm): 3.68 (s, 3H), 3.81 (s, 3H), 5.00 (s, 2H), 5.28 (s, 1H), 7.17-7.19 (m, 1H), 7.31-7.34 (m, 2H), 7.42 (m, 1H), 7.56 (s, 1H).

Compound 219: m.p. 116-118° C.

Compound 229: m.p. 124-126° C. δ(ppm): 3.88(s, 3H), 4.01(s, 3H,), 5.27(s, 2H), 6.46(s, 1H), 7.06(m, 1H), 7.21(m, 1H), 7.41(m, 5H), 7.62(m, 2H).

Compound 232: thick oil. δ(ppm): 0.93(m, 2H), 1.14(m, 2H), 1.86(m, 1H), 3.85(s, 3H), 4.00(s, 3H), 5.23(s, 2H), 6.03 (s, 1H), 7.02(m, 1H), 7.19(m, 1H), 7.30(m, 2H), 7.40(m, 2H), 7.48(m, 1H), 7.62(m, 2H).

Compound 424: m.p. 118-120° C. δ(ppm): 3.72(s, 3H), 3.82(s, 3H), 5.47(s, 2H), 6.53(s, 1H), 7.06(m, 1H), 7.33(m, 2H), 7.38(m, 3H), 7.62(m, 3H).

Compound 475: m.p. 117-119° C. δ(ppm): 2.93(d, 3H), 3.65(s, 3H), 5.45(s, 2H), 6.50(s, 1H), 7.02(m, 1H), 7.30(m, 5H), 7.49(m, 1H), 7.69(m, 2H), 8.05(s, 1H).

Compound 659: m.p. 135-137° C. δ(ppm): 3.68(s, 3H), 3.77(s, 3H), 5.38(s, 2H), 6.48(s, 1H), 6.92(m, 1H), 7.01(m, 2H), 7.20(m, 1H), 7.37(m, 2H), 7.54(m, 2H), 7.94(s, 1H).

Compound 660: m.p. 118-120° C. δ(ppm): 2.35(s, 3H), 3.66(s, 3H), 3.74(s, 3H), 5.26(s, 2H), 6.45(s, 1H), 7.08(m, 2H), 7.16(m, 1H), 7.22(m, 2H), 7.34(m, 2H), 7.38(m, 1H), 7.54(s, 1H)).

Compound 661: m.p. 147-149° C. δ(ppm): 3.75(s, 3H), 3.83(s, 3H), 5.25(s, 2H), 6.55(s, 1H), 7.01(s, 1H), 7.26(m, 1H), 7.34(m, 2H), 7.44(m, 2H), 7.63(s, 1H), 7.67(s, 1H).

Compound 662: m.p. 134-136° C. δ(ppm): 2.34(s, 3H), 3.68(s, 3H), 3.80(s, 3H), 5.35(s, 2H), 6.58(s, 1H), 7.22(m, 2H), 7.26(m, 1H), 7.37(m, 2H), 7.51(m, 1H), 7.58(s, 1H), 7.75(s, 1H), 8.42(d, 111).

Compound 663: thick oil. δ(ppm): 1.37(d, 9H), 3.72(s, 3H), 3.85(s, 3H), 5.05(s, 2H), 5.32(s, 1H), 7.21(m, 1H), 7.38 (m, 2H), 7.53(m, 1H), 7.65(s, 1H).

Compound 664: thick oil. δ(ppm): 1.00(m, 2H), 1.15(m, 2H), 1.85(m, 1H), 3.73(s, 3H), 3.80(s, 3H), 5.40(s, 2H), 6.10 (s, 1H), 7.00(m, 1H), 7.29(m, 2H), 7.37(m, 3H), 7.56(m, 1H), 7.60(m, 2H).

Compound 665: m.p. 117-119° C. δ(ppm): 0.97(m, 2H), 1.14(m, 2H), 1.84(m, 1H), 2.94(d, 3H), 3.93(s, 3H), 5.16(s, 2H), 6.04(s, 1H), 6.92(m, 1H), 7.19(m, 1H), 7.33(m, 3H), 7.49(m, 1H), 7.66(m, 2H).

Compound 666: m.p. 122-124° C. δ(ppm): 1.00(m, 2H), 1.17(m, 2H), 1.85(m, 1H), 2.91(d, 3H), 3.63(s, 3H), 5.43(s, 2H), 6.00(m, 1H), 6.10 (s, 1H), 6.95(m, 1H), 7.33(m, 5H), 7.61(m, 1H), 7.65(m, 2H).

Compound 667: m.p. 125-127° C. δ(ppm): 2.02(s, 3H), 2.36(s, 3H), 3.84(s, 3H), 4.00(s, 3H), 5.28(s, 2H), 7.00(m, 1H), 7.20(m, 1H), 7.30(m, 2H), 7.42(m, 2H), 7.52(m, 1H), 7.59(m, 2H).

Compound 668: m.p. 102-104° C. δ(ppm): 2.09(s, 3H), 2.36(s, 3H), 3.72(s, 3H), 3.79(s, 3H), 5.48(s, 2H), 7.00(m, 1H), 7.32(m, 2H), 7.38(m, 3H), 7.59(m, 3H).

Compound 669: m.p. 128-130° C. δ(ppm): 2.02(s, 3H), 2.36(s, 3H), 2.91(d, 3H), 3.63(s, 3H), 5.50(s, 2H), 6.96(m, 1H), 7.34(m, 5H), 7.55(m, 1H), 7.64(m, 2H).

Compound 670: m.p. 138-140° C. δ(ppm): 2.09(s, 3H), 2.37(s, 3H), 2.90, (d, 3H), 3.92(s, 3H), 5.24(s, 2H), 5.98(m, 1H), 6.99(m, 1H), 7.24(m, 1H), 7.38(m, 4H), 7.64(m, 2H).

Compound 671: m.p. 85-88° C. δ(ppm): 0.91(t, 3H), 1.40 (m, 4H), 2.40(s, 3H), 2.53(t, 2H), 3.69s, 3H), 3.75(s, 3H), 5.24(s, 2H), 7.01(m, 1H), 7.32(m, 5H), 7.58(m, 3H), 7.61(s, 1H).

Compound 672: m.p. 84-85° C. δ(ppm): 0.95(t, 3H), 1.38 (m, 4H), 2.38(s, 3H), 2.51(t, 2H), 3.69(s, 3H), 3.81(s, 3H), 5.27(s, 2H), 7.00(m, 1H), 7.26(m, 5H), 7.55(m, 3H), 7.73(m, 2H).

Compound 673: thick oil. δ(ppm): 0.93(t, 3H), 1.41(m, 4H), 2.40(s, 3H), 2.56(t, 2H), 3.73(s, 3H), 3.81(s, 3H), 5.47(s, 2H), 6.98(m, 1H), 7.28(m, 2H), 7.37(m, 3H), 7.58(m, 3H).

Compound 674: m.p. 110-112° C. δ(ppm): 0.93(t, 3H), 1.41(m, 4H), 2.36(s, 3H), 2.51(t, 2H), 3.93(d, 3H), 3.91(s, 3H), 5.21(s, 2H), 6.98(m, 1H), 7.38(m, 6H), 7.67(m, 2H).

Compound 675: m.p. 101-103° C. δ(ppm): 0.93(t, 3H), 1.41(m, 4H), 2.43(s, 3H), 2.52(t, 2H), 2.90(d, 3H), 3.60(s, 3H, CH₃), 5.54(s, 2H), 7.00(m, 1H), 7.38(m, 5H), 7.50(m, 1H), 7.61(m, 2H).

Compound 676: thick oil. δ(ppm): 2.33(s, 3H), 3.85(s, 3H), 4.01(s, 3H), 5.25(s, 2H), 6.03(s, 1H), 7.00(m, 1H), 7.25(m, 5H), 7.45(m, 1H), 7.59(m, 2H).

Compound 677: m.p. 89-91° C. δ(ppm): 2.35(s, 3H), 2.73 (s, 3H), 3.79(s, 3H), 5.45(s, 2H), 6.10(s, 1H), 7.00(m, 1H), 7.35(m, 5H), 7.58(m, 1H), 7.61(m, 2H).

Compound 678: m.p. 130-132° C. δ(ppm): 2.33(s, 3H), 2.93(d, 3H), 3.93(s, 3H), 5.19(s, 2H), 6.04(s, 1H), 7.00(m, 1H), 7.35(m, 5H), 7.42(m, 1H), 7.64(m, 2H).

Compound 679: m.p. 130-131° C. δ(ppm): 2.36(s, 3H), 2.90(d, 3H), 3.63(s, 3H), 5.47(s, 2H), 6.10(s, 1H), 7.00(m, 1H), 7.35(m, 5H), 7.50(m, 1H), 7.67(m, 2H).

Compound 681: m.p. 80-83° C. δ(ppm): 3.75(s, 3H), 3.89 (s, 3H), 5.32(s, 2H), 6.72(s, 1H), 7.00(m, 2H), 7.20(m, 1H), 7.35(m, 2H), 7.47(m, 2H), 7.64(s, 1H).

Compound 682: thick oil. δ(ppm): 1.24(d, 6H), 3.71(s, 3H), 3.81(s, 3H), 4.10(d, 1H), 5.28(s, 2H), 6.27(s, 1H), 7.20 (m, 1H), 7.34(m, 2H), 7.46(m, 2H), 7.58(s, 1H).

Compound 683: thick oil. δ(ppm): 3.42(s, 3H), 3.53(s, 3H), 3.67(s, 3H), 5.34(s, 2H), 6.34(s, 1H), 7.18(m, 1H), 7.33(m, 2H), 7.44(m, 2H), 7.58(s, 1H).

Compound 684: m.p. 149-151° C. δ(ppm): 3.74(s, 3H), 3.81(s, 3H), 5.35(s, 2H), 6.57(s, 1H), 7.21(m, 1H), 7.35(m, 2H), 7.48(m, 1H), 7.57(m, 2H), 7.62(s, 1H), 7.78(m, 2H).

Compound 685: m.p. 146-149° C. δ(ppm): 3.67(s, 3H), 3.75(s, 3H), 5.16(s, 2H), 6.48(s, 1H), 6.71(m, 1H), 7.00(m, 2H), 7.18(m, 2H), 7.32(m, 1H), 7.54(s, 1H).

Compound 686: m.p. 184-186° C. δ(ppm): 3.64(s, 3H), 3.70(s, 3H), 5.10(s, 2H), 6.46(s, 1H), 6.93(m, 1H), 7.25(m, 4H), 7.43(m, 2H), 7.53(s, 1H).

Compound 687: m.p. 125-126° C. δ(ppm): 3.73(s, 3H), 3.81(s, 3H), 5.31(s, 2H), 6.52(s, 1H), 7.00(m, 1H), 7.20(m, 2H), 7.35(m, 2H), 7.50(m, 2H), 7.61(s, 1H), 8.79(m, 1H).

Compound 688: m.p. 137-139° C. δ(ppm): 3.70(s, 3H), 3.78(s, 3H), 3.81(s, 3H), 5.29(s, 2H), 6.43(s, 1H), 6.90(m, 2H), 7.20(m, 2H), 7.35(m, 2H), 7.52(m, 2H), 7.58(s, 1H).

Compound 689: m.p. 136-138° C. δ(ppm): 3.72(s, 3H), 3.80(s, 3H), 5.30(s, 2H), 6.49(s, 1H), 7.03(m, 2H), 7.20(m, 1H), 7.35(m, 2H), 7.47(m, 1H), 7.57(m, 2H), 7.60(s, 1H).

Compound 690: m.p. 140-142° C. δ(ppm): 2.33(s, 3H), 3.70(s, 3H), 3.78(s, 3H), 5.31(s, 2H), 6.45(s, 1H), 7.14(m, 2H), 7.20(m, 1H), 7.35(m, 2H), 7.50(m, 3H), 7.58(s, 1H).

Compound 691: m.p. 128-130° C. δ(ppm): 3.69(s, 3H), 3.81(s, 3H), 5.36(s, 2H), 6.61(s, 1H), 7.03(m, 2H), 7.20(m, 1H), 7.29(m, 1H), 7.38(m, 2H), 7.60(s, 1H), 7.67(s, 1H), 8.82(m, 1H).

Compound 692: m.p. 94-96° C. δ(ppm): 0.55(m, 2H), 0.80 (m, 2H,), 3.69(s, 3H), 3.81(s, 3H), 5.26(s, 2H), 6.33(s, 1H), 7.19(m, 1H), 7.35(m, 2H), 7.56(m, 1H), 7.58(s, 1H).

Compound 693: m.p. 126-127° C. δ(ppm): 2.29(s, 3H), 2.33(s, 3H), 3.66(s, 3H), 3.74(s, 3H), 5.23(s, 2H), 6.4(s, 1H), 6.89(s, 1H), 7.05(m, 2H), 7.17(m, 1H), 7.33(m, 3H), 7.54(s, 1H), 7.70(d, 1H).

Compound 694: m.p. 134-136° C. δ(ppm): 3.68(s, 3H), 3.80(s, 3H), 5.35(s, 2H), 6.58(s, 1H), 7.22(m, 2H), 7.26(m, 1H), 7.37(m, 2H), 7.51(m, 1H), 7.58(s, 1H), 7.75(s, 1H), 8.42(d, 1H).

Compound 695: oil. δ(ppm): 2.29(s, 3H), 2.32(s, 3H), 3.64 (s, 3H), 3.71(s, 3H), 5.25(s, 2H), 6.43(s, 1H), 6.91(m, 2H), 7.13(m, 2H), 7.33(m, 2H), 7.53(s, 1H, CH), 7.72(s, 1H).

Compound 696: m.p. 133-135° C. δ(ppm): 3.66(s, 3H), 3.77(s, 3H), 4.70(d, 2H), 5.26(s, 2H), 6.32(s, 1H), 7.20(m, 3H), 7.35(m, 5H), 7.57(s, 1H).

Compound 697: m.p. 142-144° C. δ(ppm): 2.23(s, 3H), 2.25(s, 3H), 3.70(s, 3H), 3.78(s, 3H), 5.26(s, 2H), 6.44(s, 1H), 7.11(m, 1H), 7.20(m, 2H), 7.35(m, 2H), 7.40(m, 1H), 7.48(s, 1H), 7.53(s, 1H).

Compound 698: thick oil. δ(ppm): 3.63(s, 3H), 3.72(s, 3H), 4.80(s, 2H), 6.37(s, 1H), 6.95(m, 2H), 7.06(m, 2H), 7.40(m, 1H), 7.49(m, 1H), 7.58(s, 1H).

Compound 699: m.p. 138-140° C. δ(ppm): 2.31(s, 3H), 3.67(s, 3H), 3.76(s, 3H), 5.25(s, 2H), 6.48(s, 1H), 6.92(d, 1H), 7.20(m, 3H), 7.35(m, 2H), 7.40(m, 1H), 7.55(s, 1H), 7.82(d, 1H).

Compound 700: m.p. 122-124° C. δ(ppm): 3.64(s, 3H), 3.75(s, 3H), 4.60(d, 2H), 5.22(s, 2H), 6.32(s, 1H), 7.19(m, 1H), 7.33(m, 7H), 7.42(m, 1H), 7.58(s, 1H).

Compound 701: m.p. 136-137° C. δ(ppm): 1.30(m, 6H), 1.68(m, 4H), 2.01(m, 1H), 3.69(s, 3H), 3.81(s, 3H), 5.24(s, 2H), 6.24(s, 1H), 7.19(m, 1H), 7.35(m, 2H), 7.49(m, 1H), 7.58(s, 1H).

Compound 702: thick oil. δ(ppm): 1.23(t, 3H), 3.43(q, 2H), 3.69(s, 3H), 3.81(s, 3H), 5.28(s, 2H), 6.28(s, 1H), 7.20(m, 1H), 7.34(m, 2H), 7.48(m, 1H), 7.58(s, 1H).

Compound 703: thick oil. δ(ppm): 2.34(s, 3H), 3.70(s, 3H), 3.78(s, 3H), 5.27(s, 2H), 7.19(m, 1H,), 7.24(m, 2H), 7.34(m, 2H), 7.49(m, 1H), 7.55(m, 2H), 7.58(m, 1H).

Compound 704: thick oil. δ(ppm): 3.72(s, 3H), 3.78(s, 3H), 5.31(s, 2H), 6.51(s, 1H), 7.19(m, 1H), 7.29(m, 2H), 7.35(m, 2H), 7.48(m, 1H), 7.57(m, 2H), 7.60(m, 1H).

Compound 705: thick oil. δ(ppm): 0.97(t, 3H), 1.40(m, 2H), 1.58(m, 2H), 3.38(m, 2H), 3.69(s, 3H), 3.79(s, 3H), 5.17(s, 2H), 6.26(s, 1H), 7.18(m, 1H), 7.34(m, 2H), 7.48(m, 1H), 7.58(s, 1H).

Compound 706: m.p. 92-94° C. δ(ppm): 0.94(d 6H), 1.88 (m, 1H), 3.24(t, 2H), 3.69 (s, 3H), 3.80(s, 3H), 5.29(s, 2H), 6.26(s, 1H), 7.18(m, 1H), 7.34(m, 2H), 7.50(m, 1H), 7.58(s, 1H).

Compound 707: thick oil. δ(ppm): 0.99 (t, 3H), 1.25 (d, 3H), 1.69 (m, 2H), 3.68 (s, 3H), 3.80 (s, 3H), 4.30 (m, 1H), 5.34 (s, 2H), 6.17 (s, 1H), 7.20-7.24 (m, 1H), 7.34-7.40 (m, 2H), 7.48-7.51 (m, 1H), 7.62 (s, 1H).

Compound 708: thick oil. δ(ppm): 1.34 (t, 9H), 3.68 (s, 3H), 3.80 (s, 3H), 4.07 (m, 2H), 5.34 (s, 2H), 6.40 (s, 1H), 7.19-7.20 (m, 1H), 7.33-7.38 (m, 2H), 7.48-7.51 (m, 1H), 7.56 (m, 1H).

Compound 709: m.p. 93-95° C. δ(ppm): 1.59(m, 4H), 1.62 (m, 2H), 3.68(s, 3H), 3.77(m, 4H), 3.84(s, 3H), 5.27(s, 2H), 6.17(s, 1H), 7.19(m, 1H), 7.34(m, 2H), 7.48(m, 1H), 7.56(s, 1H).

Compound 710: m.p. 142-144° C. δ(ppm): 3.68(s, 3H), 3.75(m, 8H), 3.81(s, 3H), 5.28(s, 2H), 6.27(s, 1H), 7.19(m, 1H), 7.35(m, 2H), 7.46(m, 1H), 7.57(s, 1H).

Compound 711: thick oil. δ(ppm): 1.25(d, 6H), 2.59(m, 2H), 3.60(m, 2H), 3.68(s, 3H), 3.80(s, 3H), 4.53(m, 2H), 5.28(s, 2H), 6.24(s, 1H), 7.19(m, 1H), 7.35(m, 2H), 7.49(m, 1H), 7.56(s, 1H).

Compound 715: m.p. 115-116° C.

FORMULATION EXAMPLE

Base on 100% active ingredient (Weight/Weight %)

Example 4

30% Compound 20 wettable powders

| | |
|---|---|
| Compound 20 | 30% |
| Sodium dodecyl sulfate | 2% |
| Lignin sulfonate | 3% |
| Naphthalene sulfonic acid formaldehyde condensate | 5% |
| Precipitated calcium carbonate | Make up to 100% |

Compound 20 and other components are fully mixed, after smashing through ultrafine pulverizer, that is, 30% compound 20 wettable powders products.

Example 5

30% Compound 20 suspension concentrate

| | |
|---|---|
| Compound 20 | 40% |
| Glycol | 10% |
| Nonylphenols polyethylene glycol ether | 6% |
| Lignin sulfonate | 10% |
| Carboxymethyl cellulose | 1% |
| 37% formaldehyde aqueous solution | 0.2% |
| 75% of silicone oil water emulsion | 0.8% |
| Water | make up to 100% |

Fully mixing the compound 20 and other components, suspension concentrate can be obtained, water suspension can be diluted from the concentration of any necessary dilution.

Example 6

60% Compound 20 water dispersible granules

| | |
|---|---|
| Compound 20 | 60% |
| Naphthalene sulfonate formaldehyde condensate | 12% |
| Sodium-N-methyl-N-oleyl taurate | 8% |
| Polyvinylpyrrolidone | 2% |
| Carboxymethyl cellulose | 2% |
| Kaolin | make up to 100% |

To mix the compound 20 and other components, after smashing, kneading together with water, added to the granulation 10-100 mesh machine for granulation, then by drying and sieving (at the scope screen).

BIOLOGICAL TESTING

Example 7

Determination of Insecticidal and Acaricidal Activity

Determination of insecticidal and acaricidal activity of selected compounds were carried out by following procedure:

Compounds were dissolved in mixed solvent (acetone: methanol=1:1), and diluted to required concentration with water containing 0.1% of Tween 80.

The second instar larvae of armyworm (*Spodoptera exigua*), diamond backmoth (*Plutella xylostella*), green peach aphids (*Myzus persicae*) and mite (*Tetranychus cinnabarinus*) were used in biological test. The method was employed either spraying by airbrush. A test solution (0.5 ml) was sprayed at the pressure of 0.7 kg/cm². Percent mortality was determined after 2-3 days.

Part of Test Results:

At 600 mg/L, compound 25, 667 showed 100% control of diamond backmoth. Compound 229, 424, 475 showed 100% control of armyworm. Compounds 20, 25, 229, 682, 691, 693, 694, 697 showed 100% control of mite.

At 150 mg/L, compound 20 showed 100% control of mite.

At 40 mg/L, compound 691, 694, 701 showed 100% control of mite. Compound 682, 697 showed more than 95% control of mite.

At 5 mg/L, compound 20, 691, 694, 701 showed more than 50% control of mite.

At 10 mg/L, compound 20 showed 100% inhibition activity on carmine spider mite eggs. At 5 mg/L, compound 20 showed 80% inhibition activity on carmine spider mite eggs.

At 20 mg/L, compound 20 showed 100% control on nymph of carmine spider mite. At 10 mg/L, compound 20 showed 90% control on nymph of carmine spider mite.

Example 8

Determination of Fungicidal Activity

Determination of fungicidal activities against plant diseases of selected compounds were carried by following procedure:

Determination of Fungicidal Activity In Vitro:

Compounds were dissolved into DMSO to receive three solutions of 2000 mg/L, 667 mg/L and 222 mg/L for test. The solution for inhibition of fungal growth was added in 96 well polystyrene microtiter plates so that all wells receive 1 μl of DMSO solution of test compound, then 79 μl fungus conidial suspension were added into wells to receive the required concentration 25 mg/L, 8.3 mg/L and 2.8 mg/L respectively, which were placed into incubator. After 24 hours incubation, all plates were evaluated for inhibition percent of fungal growth.

Determination of Fungicidal Activity In Vivo:

Compounds were disolved into acetone to receive stock solution. Deionized water containing 0.1% Tween 80 was added in the previous solution to receive 20 ml test solution. Plants are sprayed by using a turntable sprayer. After 24 hours, plants were innoculated with a conidial suspension. Plants were then transferred into a dew chamber [R.H. (relative humidity)>95%] for infection. After this treatment, plants were removed from the chamber to the greenhouse for normal maintaining, After the infection period, the plants were placed in the greenhouse. After 1 week, the plants were scored for disease control.

Part of Test Results In Vitro:

At 25 mg/L, compound 19, 20, 25, 41, 232, 475, 664, 667, 668 showed 100% control of rice blast, compound 19, 20, 25, 41, 229, 232, 424, 664, 667, 668 showed 100% control of tomato late blight, compound 19, 20, 41, 667, 668 showed more than 50% control of cucumber grey mold.

At 8.3 mg/L, compound 19, 20, 666, 667, 676, 677 showed 100% control of rice blast, compound 25, 41, 229, 232, 475, 664, 665, 668, 670 showed about 80% control of rice blast.

At 2.8 mg/L, compound 19, 20 showed 100% control of rice blast, compound 41, 667, 676 showed about 80% control of rice blast, compound 667 showed about 50% control of cucumber grey mold.

Part of Test Results In Vivo:

At 400 mg/L, compound 19, 20, 25, 41, 229, 232, 424, 664, 667, 668 showed 100% control of cucumber downy mildew, compound 19, 20, 25, 41, 232, 424, 667, 668 showed 100% control of cucumber anthracnose, compound 680 showed 100% control of wheat powdery mildew, compound 19, 20, 25 showed more than 80% control of wheat powdery mildew.

At 25 mg/L, compound 19, 25, 41 showed 100% control of cucumber downy mildew, compound 19, 20, 25, 41, 665, 677, 669, 670, 678 showed 100% control of cucumber anthracnose, compound 680 showed 98% control of wheat powdery mildew, compound 19, 25, 41, 665, 669 showed 100% control of corn rust.

At 6.25 mg/L, compound 25, 665, 666, 667, 669, 678 showed more than 80% control of corn rust.

What is claimed:

1. A substituted pyrimidine ether compound having the following general formula I:

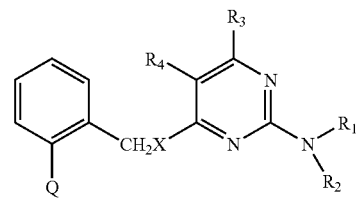

wherein:

$R_1$ is selected from H or $C_1$-$C_4$alkyl;

$R_2$ is selected from phenyl, benzyl or pyridyl; each phenyl, benzyl and pyridyl optionally substituted with 1-3 substituents independently selected from the group consisting of halogen, $NO_2$, CN, $C_1$-$C_3$alkyl, $C_1$-$C_3$haloalkyl, $C_1$-$C_3$alkoxy or $C_1$-$C_3$haloalkoxy;

$R_3$ and $R_4$ may be the same or different, selected from H, Cl, Br, $NO_2$, CN, $C_1$-$C_4$alkyl, $C_1$-$C_4$haloalkyl, $C_3$-$C_6$cycloalkyl, $C_1$-$C_3$alkoxy or $C_1$-$C_3$haloalkoxy;

X is O or S;

Q is

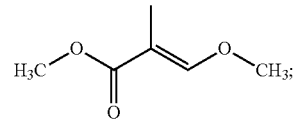

or a salt or a stereoisomer thereof.

2. The compound according to claim 1, wherein
$R_1$ is H or methyl;

$R_2$ is phenyl or pyridyl; each phenyl and pyridyl optionally substituted with 1-3 substituents independently selected from the group consisting of halogen, CN, $C_1$-$C_3$alkyl, $C_1$-$C_3$haloalkyl, $C_1$-$C_3$alkoxy or $C_1$-$C_3$haloalkoxy;

$R_3$ is selected from H, Cl, Br, methyl, cyclopropyl or $CF_3$;

$R_4$ is selected from H, Cl, Br, $CH_3$ or CN;

X is O; and wherein the salt is formed with hydrochlorides, phosphates, acetic acid, benzenesulfonic acid or oxalic acid.

3. The compound according to claim 2, wherein $R_1$ is H;

$R_2$ is phenyl or pyridyl; each phenyl and pyridyl optionally substituted with 1-3 substituents independently selected from the group consisting of Cl, F, CN, methyl, $CF_3$, $OCH_3$ or $OCF_3$;

$R_3$ is selected from methyl, cyclopropyl or $CF_3$; and $R_4$ is selected from H, Cl or $CH_3$.

4. A composition of insecticides, acaricides and fungicides which comprises a compound according to claim 1 as an active ingredient, wherein the weight percentage of the active ingredient in the composition is from 0.5-90%.

* * * * *